United States Patent
Ahn

(10) Patent No.: US 10,413,231 B2
(45) Date of Patent: Sep. 17, 2019

(54) ORIFICE PROBE APPARATUS AND A METHOD OF USE THEREOF

(76) Inventor: Nicholas Ahn, Shaker Heights, OH (US)

( * ) Notice: Subject to any disclaimer, the term of this patent is extended or adjusted under 35 U.S.C. 154(b) by 0 days.

(21) Appl. No.: 13/386,300

(22) PCT Filed: Jul. 23, 2010

(86) PCT No.: PCT/US2010/002086
§ 371 (c)(1),
(2), (4) Date: Jan. 20, 2012

(87) PCT Pub. No.: WO2011/011085
PCT Pub. Date: Jan. 27, 2011

(65) Prior Publication Data
US 2012/0130281 A1    May 24, 2012

Related U.S. Application Data

(60) Provisional application No. 61/271,606, filed on Jul. 23, 2009.

(51) Int. Cl.
| A61B 5/00 | (2006.01) |
| A61B 5/22 | (2006.01) |
| A61B 90/98 | (2016.01) |

(52) U.S. Cl.
CPC ............. *A61B 5/42* (2013.01); *A61B 5/227* (2013.01); *A61B 5/4255* (2013.01); *A61B 5/4381* (2013.01); *A61B 5/4827* (2013.01); *A61B 90/98* (2016.02); *A61B 5/483* (2013.01)

(58) Field of Classification Search
CPC ...... A61B 5/4528; A61B 5/103; A61B 5/0053
USPC ............................................. 33/512; 600/587
See application file for complete search history.

(56) References Cited

U.S. PATENT DOCUMENTS

| 5,385,577 A | 1/1995 | Maurer et al. |
| 5,452,719 A | 9/1995 | Eisman et al. |
| 5,533,515 A | 7/1996 | Coller et al. |
| 5,662,699 A | 9/1997 | Hamedi et al. |
| 5,924,984 A * | 7/1999 | Rao .............................. 600/373 |
| 6,001,060 A | 12/1999 | Churchill et al. |
| 6,142,959 A | 11/2000 | Sarvazyan et al. |
| 6,171,259 B1 | 1/2001 | Fisher |
| 6,625,495 B1 | 9/2003 | Alon et al. |

(Continued)

FOREIGN PATENT DOCUMENTS

| JP | 61-76129 | 4/1986 |
| JP | 2003505134 A | 2/2003 |
| WO | WO 2007/101861 | 9/2007 |

OTHER PUBLICATIONS http://web.archive.org/web/20080802124549re_/www.emedicinehealth.com/cuada_equina_syndrome/page5_em.htm; Cauda Equina Syndrome by WebMD. Published Aug. 2008. Accessed Sep. 2010. p. 5.

(Continued)

*Primary Examiner* — Daniel L Cerioni

(57) ABSTRACT

An orifice probe, particularly for detecting if a patient has or has a risk of having cauda equina syndrome and a method for using same, the probe having a body for insertion into the anus of a patient, a sensing device for measuring at least one of the rectal tone and perianal or rectal sensation, and an output device for yielding at least one of the measurement of the rectal tone of the patient and whether the patient has perianal or rectal sensation.

59 Claims, 12 Drawing Sheets

(56) References Cited

U.S. PATENT DOCUMENTS

| | | |
|---|---|---|
| 7,485,099 B2 | 2/2009 | Benderev |
| 7,678,064 B2 | 3/2010 | Kuban |
| 2004/0054392 A1 | 3/2004 | Dijkman |
| 2005/0010129 A1* | 1/2005 | Bleustein et al. ............ 600/555 |
| 2005/0043599 A1 | 2/2005 | O'Mara |
| 2006/0247725 A1* | 11/2006 | Gerber et al. .................. 607/41 |
| 2007/0083238 A1* | 4/2007 | Brockman ......... A61N 1/36007 607/1 |
| 2009/0005707 A1* | 1/2009 | Sarvazyan et al. ........... 600/587 |
| 2009/0023992 A1 | 1/2009 | Gilad et al. |
| 2009/0082702 A1 | 3/2009 | Folkerts et al. |
| 2009/0177094 A1 | 7/2009 | Brown et al. |

OTHER PUBLICATIONS

Ahn, U.M., Ahn, N.U., Buchowski, J.M., Garrett, E.S., Sieber, A.N., Kostuik J.P., "Cauda equina syndrome secondary to lumbar disk herniation: a meta-analysis of surgical outcomes," *Spine* (Phila., Pa., 1976). Jun. 15, 2000; 25(12):1515-22.

Ho, Dan-Phuong Ester N., "A Case Study of Cauda Equina Syndrome," *The Permanente Journal*, Fall, 2003, vol. 7, No. 4.

Small, Stephen A. et al., Orthopedic pitfalls: cauda equina syndrome, American Journal of Emergency Medicine (2005), 23, 159-163.

\* cited by examiner

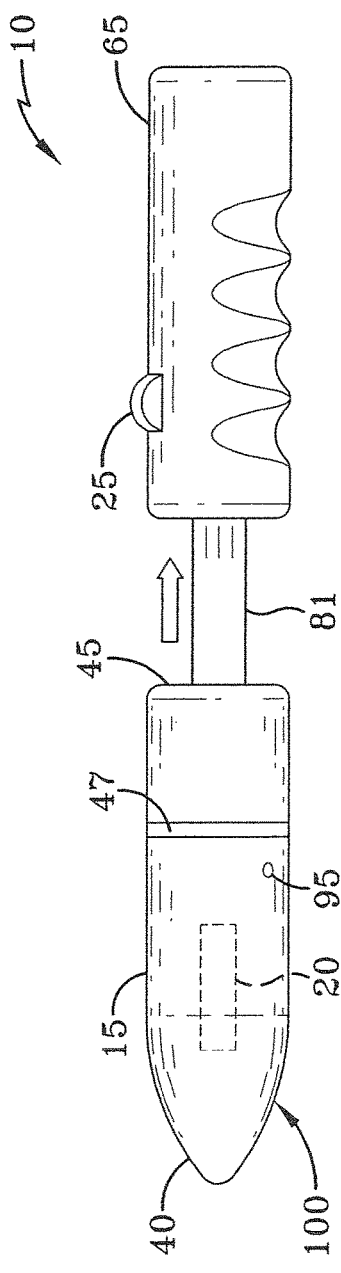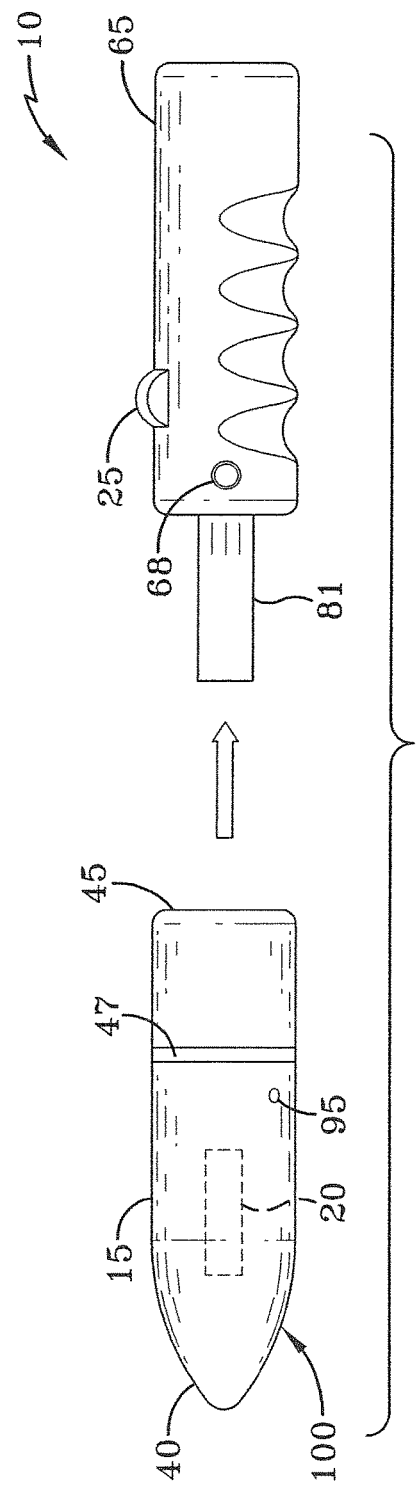

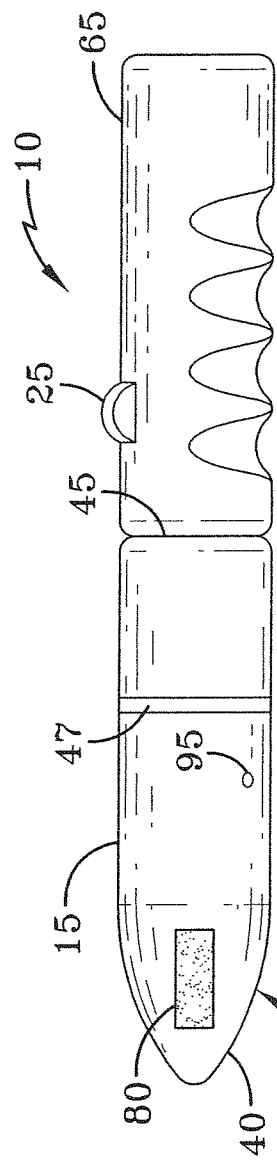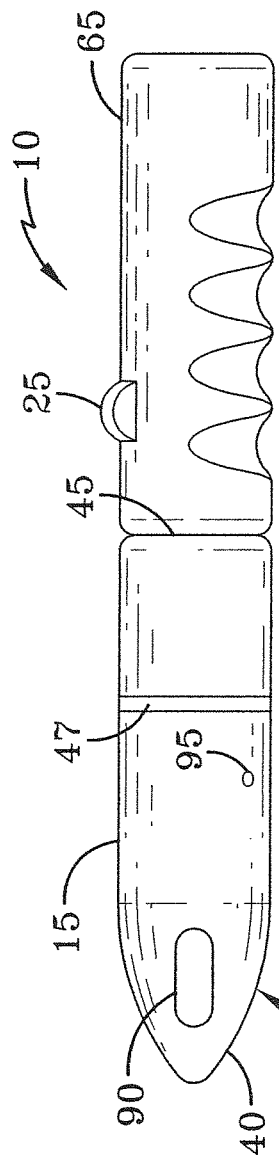
FIG-13
FIG-14

ORIFICE PROBE APPARATUS AND A METHOD OF USE THEREOF

CROSS-REFERENCE TO RELATED APPLICATIONS

This application claims priority of U.S. Provisional Patent Application Ser. No. 61/271,606 filed Jul. 23, 2009, the subject matter of which is incorporated herein by reference in its entirety.

BACKGROUND OF THE INVENTION

Field of the Invention

The present invention relates generally to an orifice probe apparatus, and more particularly, to a rectal probe apparatus for use in diagnostic procedures as well as methods for the use of such probes probe apparatus.

Description of the Prior Art

As an extension of the brain, the nerve roots send and receive messages to and from the pelvic organs and lower limbs. FIG. 1 shows an approximate top view of a vertebra with the cauda equina (a bundle of nerves that extends from the base of the spinal cord through the central spinal canal) shown in cross section and two nerve roots exiting the central spinal canal and extending through intervertebral foramina on either side of the vertebra. The spinal cord and cauda equina run vertically along the spine through the central spinal canal, while nerve roots branch off of the spinal cord and cauda equina between adjacent vertebrae and extend through the intervertebral foramina.

Cauda equina syndrome is a condition in which there is severe neural compression of the lumbar or lumbosacral spine such that the sacral roots become non-functional and the patient loses control of the bowel and bladder. Other manifestations of cauda equina syndrome can include saddle anesthesia or radiating pain down the lower extremities with associated weakness or numbness. However, the hallmark of cauda equina syndrome is severe neural compression below the conus causing frank loss of bowel and bladder control. This can manifest itself either with urinary retention and inability to urinate with severe pain from bladder expansion, or frank loss of bowel and bladder control causing the patient to either urinate or defecate on himself or herself without realizing that this has occurred. The fact that saddle anesthesia is often present would also cause the patient to not realize that such an accident had happened.

Lower back pain is common and usually resolves with non-operative care. When stenosis, or nerve compression, is present however the patient will often experience severe pain radiating into the lower extremities following the distribution of the nerves being compressed. The patient may also experience weakness, numbness, and/or tingling with difficulty walking or standing. Surgical management in the form of a decompression to take the pressure off of the nerves that are being compressed or crushed may be required in these cases to alleviate the patient's neurogenic symptoms.

Despite this, however, even cases of stenosis, or nerve compression, are not true surgical emergencies. In general there is not felt to be a rush for surgery and the appropriate time to treat neural compression in the lumbar spine surgically is when the patient's quality of life has reached a point where it is unacceptable and when all reasonable non-operative treatments have failed. If surgery is performed to decompress the lumbar neural elements the success rates are excellent, in the 85-90% range for improvement of neurogenic symptoms. It is not until the condition has been present for over two years that a decline in success rates was noted and even in these cases the decline is only by approximately 10%. Thus, if the condition has been present for over two years, the success rates would still be in the 75-80% range. As such, patients are typically advised that surgery for stenosis is a "quality of life" issue that the patient considers when he or she is ready and wishes to proceed.

However, the one lumbar condition that would be considered a surgical emergency is cauda equina syndrome. Cauda equina syndrome is relatively rare, encompassing less than 1-2% of cases of stenosis. However, when present, this is a true surgical emergency, and surgery that is not performed on an emergent basis has been found to lead to a dramatic decrease in success rates and postoperative function. Because regaining the ability to control one's bowel and bladder is universally accepted as being very important, surgery is recommended to give the patient the best chance of regaining this important function. A recent study by Ahn et al., Spine, 1999, demonstrated that if decompression surgery was performed within 48 hours, that this affords the patient the best chance of improvement of return of bowel and bladder control in the 80% range. If one waits beyond 48 hours to perform the decompression, the success rates fall to approximately 50-60%. {Ahn, U. M., Ahn, N. U., Buchowski, J. M., Garrett, E. S., Sieber, A. N., Kostuik J. P., "Cauda equina syndrome secondary to lumbar disk herniation: a meta-analysis of surgical outcomes," Spine (Phila., Pa., 1976). 2000 Jun. 15; 25(12):1515-22.} Thus, cauda equina syndrome is considered a true surgical emergency.

The causes of cauda equina syndrome can include, but are not limited to, a massive herniated disk, severe spinal stenosis, spondylolisthesis, or any mass such as a tumor or infection causing severe nerve compression. However, regardless of the cause, the common thread is that there is severe nerve compression below the conus causing the sacral roots to shut down with loss of bowel and bladder control.

The most common cause of cauda equina syndrome is a lumbar disk herniation causing excessive compression on the cauda equina. Cauda equina syndrome is relatively uncommon with an incidence of approximately 1-2% of all herniated lumbar disks. The results of cauda equina syndrome are often very serious, being both painful and having many debilitating effects. These include life-sustaining disabilities including bowel and bladder incontinence, leg weakness, gait abnormality, painful paresthesias, urinary retention, genito-urinary deficits, including numbness in the buttocks, the vagina (of a woman), neurogenic bladder dysfunction, neuropathic pain, which can be paralyzing, sexual dysfunction and inability (of a woman) to have children. Although cauda equina syndrome is an uncommon occurrence, this condition can be encountered by any physician since lumbar spinal stenosis and lumbar disk herniations are very common.

Because this is considered an emergent situation, a great number of lawsuits have arisen due to "missed" cauda equina syndrome. As noted above, even though stenosis or nerve compression is present, cauda equina syndrome is only present if there is a loss of functioning of the bowel and bladder. The hallmark of determining if an individual has cauda equina syndrome, however, is not based on the patient's subjective complaints but rather on a rectal examination. Typically, the clinician will insert a gloved finger into the anus and subjectively measure tone, volition and perianal sensation. However these are subjective measurements and there is no objective measure as to what normal tone and volition would be. In addition, based on the clinician's experience, different opinions can be generated. Furthermore, because cauda equina syndrome is relatively rare, many clinicians may not have experience with a truly abnormal rectal exam in which the tone is diminished or absent. For example, even if the patient has minimal or no anal tone, the patient can press the gluteal muscles together giving the appearance that tone or volition is present when it really is not.

Perianal or rectal sensation may also be measured by the clinician by applying a stimulus or stimuli to the perianal or rectal area of the patient, for example, pinprick from a safety pin applied to the perianal area on both the patient's right and left sides. A reduced or lack of sensation reported by the patient in response to the perianal pinprick indicates to the clinician that the patient may be at risk of cauda equina syndrome. Perianal sensation is often difficult to test. Patients are in pain and are usually very uncooperative. Moreover, the patient has to be rolled over in order to make the patient's anus accessible. Without the cooperation of the patient, it is difficult to position the patient properly. Some patients are unable to express as to whether or not they have reduced or no perianal sensation, such as patients who are suffering from dementia. Therefore, perianal sensation is oftentimes not measured. This is problematic because the hallmark of determining if neurologic function is present includes both motor and a sensory examination. Further, the conventional perianal sensory pinprick tests also suffer from a variety of deficiencies. Such deficiencies include, but are not limited to, difficulty in accessing the perianal area with a safety pin and applying the appropriate force when pricking the perianal area with the safety pin.

Thus, cauda equina syndrome is a relatively uncommon condition. It is usually associated with a large, space-occupying lesion within the canal of the lumbosacral spine. As noted above, cauda equina syndrome can be characterized by low back pain, sciatica, lower extremity sensory motor loss and bowel and bladder dysfunction, but it is the loss of bowel and bladder function that defines this condition and separates it as a true surgical emergency.

The initial signs and symptoms of cauda equina syndrome can be subtle, and include saddle anesthesia of the perineum, urinary retention, numbness, bilateral lower extremity pain and weakness. Cauda equina syndrome is often overlooked since a great many patients under primary and emergency care of physicians have low back pain and sciatica and since cauda equina syndrome is rare. Due to the great frequency of lumbar disorders, and overall rarity of cauda equina syndrome, it is common for clinicians to overlook this condition.

Although cauda equina syndrome accounts for a small minority of cases of lumbar disease, therefore, the overall frequency of lumbar disorders in general means that this condition does occur with reasonable frequency and may be encountered by any physician. Thus, cauda equina syndrome is considered a condition in which every physician should be familiar and also one in which is it considered unacceptable practice if it is missed. It is considered below the standard of care for any physician to miss this condition and delay the emergent surgical treatment for this problem.

Due to these and other deficiencies of such conventional screening techniques and the severity of the outcome if improperly diagnosed, physicians routinely rely on MRI (magnetic resonance imaging) scans or CT myelograms (in patients who cannot undergo MRI) to rule out this condition by ruling out severe neural compression. However, cauda equina syndrome is rare and such procedures are expensive and cumbersome, particularly when ordered after hours in an emergency room situation. Due to the perceived rarity of cauda equina syndrome, there has been no practical probe developed for routine examination for cauda equina syndrome, resulting in missing the occurrence of this syndrome. When a missed cauda equina syndrome does occur, and surgical management is delayed, the success rates for recovery of bowel and bladder dysfunction are significantly diminished. This in turn may result in unfortunate and expensive treatments, as well as huge awards from medical malpractice lawsuits.

Cauda equina syndrome is considered a surgical emergency of which every physician is expected to be aware. The inventor performed a preliminary review of seven cases decided in the U.S. courts related to cauda equina syndrome. The cases reviewed are the following: *Rutledge & Rutledge v USA*, Civil Case #06-00008, 2008 W, 2008 WL 3914965 (D. Guam 2008); *William Owen v USA*, Civil Case #07-4014-KES, 2008 WL 5122282 (D. S.D. 2008); *Dollard v Allen, Whip, LVMC*, Civil Case #02-CV-87-B, 2005 WL 2007028; *Jimerson v USA*, Civil Case #99-CV-0954E(Sr), 30 ILR 3164 (N.D. N.Y. 2003; *Kling & Kling v Disclafani et. al.*, Case No. 5D07-2019, (Fl. Dist. Ct. App. 2008); *Skrzypchak & Skrzypchak v Paul Jensen et. al.*, Appeal Nos. 2007AP2729, 2008AP154, (Wi. Ct. App. 2009); and *Stitt v Dept. of Corrections State of Georgia et. al.* (250 Ga. App. 420, 551 S.E.2d 793 (2001)). Of these seven cases, four resulted in a verdict for the plaintiff, with judgements ranging from $500,000.00 to $7,502,674.00. Thus, the huge settlements in these cases highlights the importance of being able to determine the presence of cauda equina syndrome not only to give the patient the best chance of recovery of bowel and bladder control but also to protect the provider and institution from possible legal ramifications.

A study of these cases demonstrated that time to diagnosis and surgery ranged from under 24 hours to over one month, and did not predict which cases would rule for the plaintiff. Severity of initial symptoms also did not predict which cases would rule for the plaintiff. The one common thread in all cases in which a judgement was ruled for the plaintiff was that no rectal examination was performed by the treating providers. This was consistently considered a significant factor in determining failure to provide the standard of care.

As noted previously, a study by Ahn et. al ["Cauda equina syndrome secondary to lumbar disc herniation: a meta-analysis of surgical outcomes," Ahn U M, Ahn N U, Buchowski J M, Garrett E S, Sieber A N, Kostuik J P, *Spine* (Phila Pa. 1976). 2000 Jun. 15; 25(12):1515-22.] demonstrated that, if surgery is performed within 48 hours of onset of cauda equina syndrome, the success rates for return of bowel and bladder control are significantly higher than if surgery was performed after 48 hours. This study also demonstrated that for all cases performed within 48 hours there was no difference in success rates, and that for all cases performed after 48 hours there was no difference in success rates. Scientifically, therefore, time to surgery has been the only factor which has been shown to influence outcomes for patients with cauda equina syndrome. Nevertheless, time to surgery weighed very little on the verdicts which were handed down. It was the lack of an adequate rectal examination which appeared to carry the most weight in determining guilt in these cases.

In the case of *Rutledge & Rutledge v USA*, Civil Case #06-00008, 2008 WL 3914966 (D. Guam 2008), in which a judgment for the plaintiff of $7,502,674 was granted, the defendant successfully sued the VA Medical System (and thus the U.S. government) even though the claimant only complained of back pain and vague vaginal symptoms on initial presentation. The claimant did not complain of any bowel or bladder changes, nor did the claimant complain of true saddle anesthesia or lower extremity symptoms that would make the clinician suspicious for cauda equina syndrome. Thus, the defendant did not have any of the typical signs or symptoms of cauda equina syndrome and certainly did not have a loss of bowel or bladder control on initial presentation. It was not until 30 days later that she actually presented with true loss of bladder control, and at that point imaging studies were performed emergently and surgery was performed within 24 hours. Despite the fact that the claimant appeared to have received adequate care, the fact that a rectal examination was not performed on initial presentation, even though the symptoms were atypical for cauda equina syndrome, made a huge impact on the overall outcome of the case with an enormous penalty attributed to the treating providers for not having checked rectal tone. This highlights the importance of a good rectal exam in treating any patient with lumbar symptoms. A knowledge of cauda equina syndrome and that this condition is an emergency is expected of all providers.

However, cauda equina syndrome is also very rare, and even the busy spinal surgeon will only see one or two cases per year. This calls into question the legitimacy of the rectal examination particularly when performed by a clinician who has not seen patients with this condition and is not familiar with spinal disorders. This is a primary impediment to performing an adequate rectal examination that was frequently cited in these cases; that the treating provider was not a specialist and would not know if the rectal exam was truly abnormal or not. That said, this proved to be an inadequate defense in these cases.

Having a device designed to specifically rule out cauda equina syndrome would therefore be invaluable to the treating provider as well as to the institution at which the provider works as it would allow for an adequate defense should a patient argue that the presence of cauda equina syndrome was "missed". Furthermore, having a device which would objectively give a value to definitively determine if the rectal tone is within normal limits or concerning would allow the clinician to freely discharge certain patients with follow up while still protecting the provider and the institution from potential claims.

It is not reasonable for the treating provider to consult a spinal surgeon for every single patient with lumbar complaints, as back pain is second only to upper respiratory infections for reasons that patients see their primary care physicians. It is also not reasonable from a cost perspective to order an MRI on every patient with lumbar complaints. A simple inexpensive device to rule out this potentially devastating condition is thus necessary and not currently available.

Therefore, it would be desirable to provide a probe and accessories wed with the probe (referred to as "probe apparatus") and a method of using the probe to diagnose cauda equina syndrome. Having a probe apparatus which would allow an objective measure of normal anal/rectal tone would be of great benefit in providing medical diagnosis in a patient with low back pain or neurogenic symptoms in terms of ruling out cauda equina syndrome, particularly in an emergency room environment. Furthermore, having a probe apparatus that would allow for a definitive sensory evaluation to be performed would also be of great benefit. Such probes probe apparatus would be considered more sanitary, both for the clinician as well as for the patient and would provide more of an objective measure to provide a more definitive method of assuring that this devastating condition is not present for the patient. It would be especially beneficial if such probe apparatus could be developed which is relatively inexpensive to manufacture, is disposable after use, and is reliable in detecting cauda equina syndrome.

Cauda equina syndrome also occurs in animals, and especially in dogs, particularly dachshunds. Because dachshunds are afflicted with the same genetic disorder causing Achondroplasia in humans, they are subject to same severe spinal stenosis that Achondroplasts typically suffer from due to a congenitally small spinal canal when middle-adulthood is reached. The most common symptom is pain, particularly pain in the back, on one or both hind legs, or tail; however, because an animal cannot report symptoms it is frequently difficult to determine if the stenosis has become severe. The condition usually progresses until the dog has become completely incontinent and has lost function in the lower extremities; specialized wheel-walkers for dachshunds have been manufactured because lower extremity paralysis occurs so frequently in these dogs. Currently, diagnoses are made by checking the reflexes, a neurological exam and performing a myelogram (i.e., injecting dye and performing plain films). However, it is difficult to perform a neurologic examination in a dog that cannot follow commands, and reflexes have poor sensitivity and specificity in determining if severe stenosis is present. Furthermore, myelography is painful, has associated risks, and is expensive and invasive and as such is a poor tool for routine screening. Although it would alert the owner and veterinarian that impending or significant neurologic compromise is occurring, an anal exam is not typically performed on a routine basis in these dogs, even when they have reached an age where severe stenosis and loss of neurologic function is common. Since the invention disclosed herein can be used both on humans and on animals, the term "patient" as used herein applies both to humans and animals.

It should also be noted that extrinsic compression occurring at the conus medullaris or the spinal cord itself can also cause changes in, or a loss of bowel and/or bladder function. Thus, while compression of the cauda equina is the most frequent cause of loss of bowel and/or bladder function occurring from extrinsic neural compression, the physician must also be aware that compression higher in the neural axis can also lead to alterations in bowel and/or bladder function as well. For the purposes of this application, any condition in which extrinsic neural compression leads to an alteration in bowel or bladder function, such as cauda equina syndrome, conus medullaris syndrome, or spinal cord compression will be termed "cauda equina syndrome."

A health problem which many physicians must be aware of is the enlargement and changes in the normal shape of a man's prostate gland which may be an indication of urinary symptoms and prostate cancer. The first examination, which is usually the first test done, is the digital rectal examination. In this examination, the doctor inserts a gloved finger into the rectum and feels the part of the prostate next to the rectum. This examination gives the doctor a general idea of the size and condition of the gland. This is a subjective test, and depending on the person applying the test, indicates its accuracy. Although it is usually just an initial test to determine whether further tests should be made, the skipping of the test or a misjudgment of the test results could lead to dire consequences. If there is a suspicion that prostate cancer has occurred, a probe can be inserted into the rectum for directing sound waves at the prostate. The echo patterns of the sound waves form an image of the prostate gland on the display screen indicating whether or not a tumor may be present. If a tumor is suspected, a biopsy is usually used to remove prostate tissue for examination under a microscope. This same condition could apply to males of many animals.

A number of devices have been developed for measuring specialized muscle function. In U.S. Pat. No. 5,452,719 (Eisman et al., 1995), an electrode is discussed for providing independent myographic data revealing the interaction and coordination of different muscles of the anal canal group. It employs activities of the separate muscle groups within a narrow time resolution. It involves the use of a pair of electrodes positioned on the outer surface of the insulating support for receiving myographic signals from the distal muscles of the canal and a second electrode spaced from the first electrode to receive myographic signals from the proximal muscles of the canal to provide data for the distal and proximal portions of the anal canal. U.S. Pat. No. 5,533,515 (Coller et al., 1996) relates to a sphincter myometer that includes a solid-state probe for the measurement and mapping of constriction pressure applied by the inner surface of a sphincter, or other portion of a body lumen, to the outer surface of the solid-state probe. Referring next to U.S. Pat. No. 7,485,099 (Benderev, 2009), this patent discloses a balloon-like sack holding a material for supporting the membrane to maintain a specific volume or to maintain a generally expansive state from which it is collapsible once a threshold amount of pressure is applied to the sack to enable a surgeon to position an implant, tissue, sling or graft. U.S. Patent Publication No. US 2009/0082702 A1 (Folkerts et al, 2009) relates to an electromechanical probe for stimulating the bulbospongiosus muscle and identifying the time of the stimulation so that the electrical responses from electrodes on the patient's skin can be identified for analysis. There is disclosed a screening system for measuring the bulbocavernosus reflex response when the reflex is induced from the activation of the bulbospongiosus superficial muscle of the perineum via mechanical stimulation of the clitoris or penis. The resulting reflex measurements can be used to detect abnormalities of the bulbocavernosus. In U.S. Pat. No. 7,678,064 (Kuban, 2010) apparatus is disclosed for allegedly detecting tactile sensitivity of a patient by applying pressure to the patient's body and determining the lowest amount of pressure that the patient can feel and/or the highest amount of pressure that the patient can tolerate.

U.S. Patent Publication US 2004/0054392 (Dijkman 2004) describes a probe for treating urinary and faecal incontinence, having a hollow body formed by flexible walls which transfer pressure on the walls to the interior of the probe, and a pressure sensor in the probe's interior for determining the pressure. Electrodes are located on the outer surface of the probe. The electrodes are used for electro-stimulation and measuring EMG activity. Dijkman has nothing to do with cauda equina syndrome and makes no measurement which could be used to readily indicate whether or not a person has a risk of having cauda equina syndrome, or whether any particular pressure is detected. U.S. Pat. No. 5,385,877 (Maurer et al. 1995) describes an electrode for activating pelvic reflexes for incontinence and has a flexible and anatomically-correct handle member connected to the distal end of a tubular member to properly position an electrode within a patient's rectum and prevents movement of the treated electrode. It has no relationship to the diagnosis or treatment of cauda equina syndrome. U.S. Patent Publication US 2005/0043599 (O'Mara 2005) discusses utilizing a pulse oximeter in the rectal cavity for the purpose of measuring oxygen saturation and other measurements consistent with pulse oximetry. O'Mara does not determine perianal or rectal sensation, and there is no mention that O'Mara's product can be used to determine if a patient has abnormal or absent sensation such as what would be encountered with cauda equina syndrome. None of the foregoing patents provide a system for determining cauda equina syndrome or apparatus for quickly and accurately determining if the foregoing syndrome is present or there is a risk that it is present.

"Cauda Equina Syndrome" in eMedicineHealth, Aug. 2, 2008, describes a standard diagnosis of cauda equina syndrome. Cauda Equina Syndrome has been described since at least as early as 1944, where a report in a medical journal was published: "Cauda Equina Compression Syndrome With Herniated Nucleus Pulposus, A Report of Eight Cases," French J D, Payne J T, *Ann. Surg.* 1944 July; 120(1):73-87. However, no single device is known which specifically determines if a patient has cauda equina syndrome.

SUMMARY OF THE INVENTION

It is an object of the present invention to provide a device to determine if a patient has or has a risk of having cauda equina syndrome.

Another object of the present invention is to provide a device for routinely determining if a patient has or has a risk of having cauda equina syndrome.

It is yet another object of the present invention to provide a probe apparatus for quickly and easily determining if a patient has or has a risk of having cauda equina syndrome.

It is still an additional object of the present invention to provide a probe apparatus for determining if a patient has or has a risk of having cauda equina syndrome.

A further object of the present invention is to provide a probe apparatus for routinely determining if a patient has or has a risk of having cauda equina syndrome.

It is yet still another object of the present invention to determine in a routine, fast and effective manner if a patient has or has the risk of having cauda equina syndrome.

Yet still an additional object of the present invention is to provide a probe apparatus for measuring the rectal tone of a patient to determine if the patient has or has the risk of having cauda equina syndrome.

A further object of the invention is the provision of a probe for insertion into the anus of a patient for easily and quickly determining if a patient has perianal sensation.

Another additional object of the present invention is to provide a probe apparatus having a probe for insertion into the anus of a patient at a proper depth to determine the rectal tone of the patient and to determine if the patient has perianal sensation, to determine if the patient has or has the risk of having cauda equina syndrome.

A yet additional object of the present invention is to provide a probe for insertion into the anus of a patient to measure the rectal temperature of the patient.

An additional object of the present invention is to provide a probe for insertion into the anus of a patient that will allow for fecal occult blood testing.

It is also still another object of the present invention to provide a probe for insertion into the anus of a patient to impose one of various perianal and/or rectal-causing stimulus/stimuli to the patient to see if the stimulus/stimuli is picked up by the patient to determine the perianal and/or rectal sensation of the patient.

An additional object of the present invention is to provide a probe for insertion into the anus of a patient to make one or more measurements and to provide a device for making those measurements available to an examiner in a meaningful form.

It is also an object of the present invention to provide a probe for insertion into the anus of a patient with structure for enabling the easy insertion and withdrawal of the probe.

Another object of the present invention is to provide a method for easily, effectively and economically determining if a patient has or has a risk of having cauda equina syndrome.

It is also a further object of the present invention to provide a method for routinely determining if a patient has cauda equina syndrome.

Another object of the present invention is to provide a probe of a probe apparatus for insertion into an orifice of a patient to determine the pressure exerted by the surfaces defining the orifice.

Another object of the present invention is to provide a probe for routinely determining the topography of a male patient's prostate gland, "topography" referring to the size of the prostate gland (to see if it is enlarged) or irregularities which could, for example, relate to prostate cancer.

It is a further object of the present invention to provide a probe apparatus for making combined examinations of a male patient's rectum to determine if the patient has a risk of having cauda equina syndrome and having irregularities and/or enlargement in the prostate gland.

Still yet another object is to provide a probe apparatus having a probe for insertion into the anus of a male patient, where the probe apparatus generates a topography signal to the patient's prostate and includes (as part of the probe or remote from the probe) topography-indicating apparatus for measuring the effect of the topography of the prostate on the signal to indicate the topography of the prostate.

The preferred embodiments also include separate probes for separately and independently measuring the rectal tone of a patient and for determining perianal sensation.

These and other objects will be determined from the description to follow and from the appended claims.

The foregoing objects are achieved according to a preferred embodiment of the invention by the provision of a probe apparatus for insertion into the anus of a patient. As used herein, the word "probe" refers to the device inserted into the anus of a patient, and the words "probe apparatus" include the inventive probe and anything used in conjunction with the probe, such as a handle and other components remote from the probe. The probe has features for measuring the rectal tone of the patient and structure for applying perianal and/or rectal-evoking stimulus/stimuli to the perianal part of the patient's anus or to the rectal area to determine if the patient has perianal and/or rectal sensation. Where only the term "perianal" is used herein, "perianal" is defined as including "or rectal"; likewise, where only the term "rectal" is used herein, "rectal" is defined as including "or perianal". Rectal tone includes one or both of resting tone and volition, and is used that way hereinafter. Rectal tone usually refers to the measurement of the force or pressure of the sphincter muscle, but it can also relate to an electrical charge for measurement of the tone, which is called "rectal function." As used herein, rectal tone includes rectal function. The determination of the rectal tone and of the perianal sensation enables the patient's examiner to determine if the patient has or has the risk of having cauda equina syndrome. Structure is provided operatively connected to the probe for establishing the depth of insertion of the probe into the patient's anus, for putting a device for determining if the patient has perianal sensation between active and inactive conditions, the rectal temperature, the presence of occult fecal blood, and for relaying the measured values to the examiner in an understandable form.

BRIEF DESCRIPTION OF THE DRAWINGS

Objects and advantages, together with the operation of the invention, may be better understood by reference to the following detailed description taken in connection with the following illustrations, wherein:

FIG. 7 is a side view of a probe apparatus incorporating the probe shown in FIGS. 3-5 having a handle.

FIG. 8 is a side view of the a probe apparatus having the probe shown in FIGS. 3-6 having a handle removably secured to the body of the probe.

FIG. 13 is a side view of a probe apparatus according to a preferred embodiment of the invention with a diagnostic element and a thermometer.

FIG. 14 is a side view of another variation of the preferred embodiment of the invention of a probe apparatus including a probe with an irregularity detector and a thermometer.

DETAILED DESCRIPTION OF THE PREFERRED EMBODIMENTS

While the present invention is described with reference to preferred embodiments described herein, it should be clear that the present invention is not limited to such embodiments. Therefore, the description of the embodiments herein is merely illustrative of the present invention and will not limit the scope of the invention.

Figure 1:
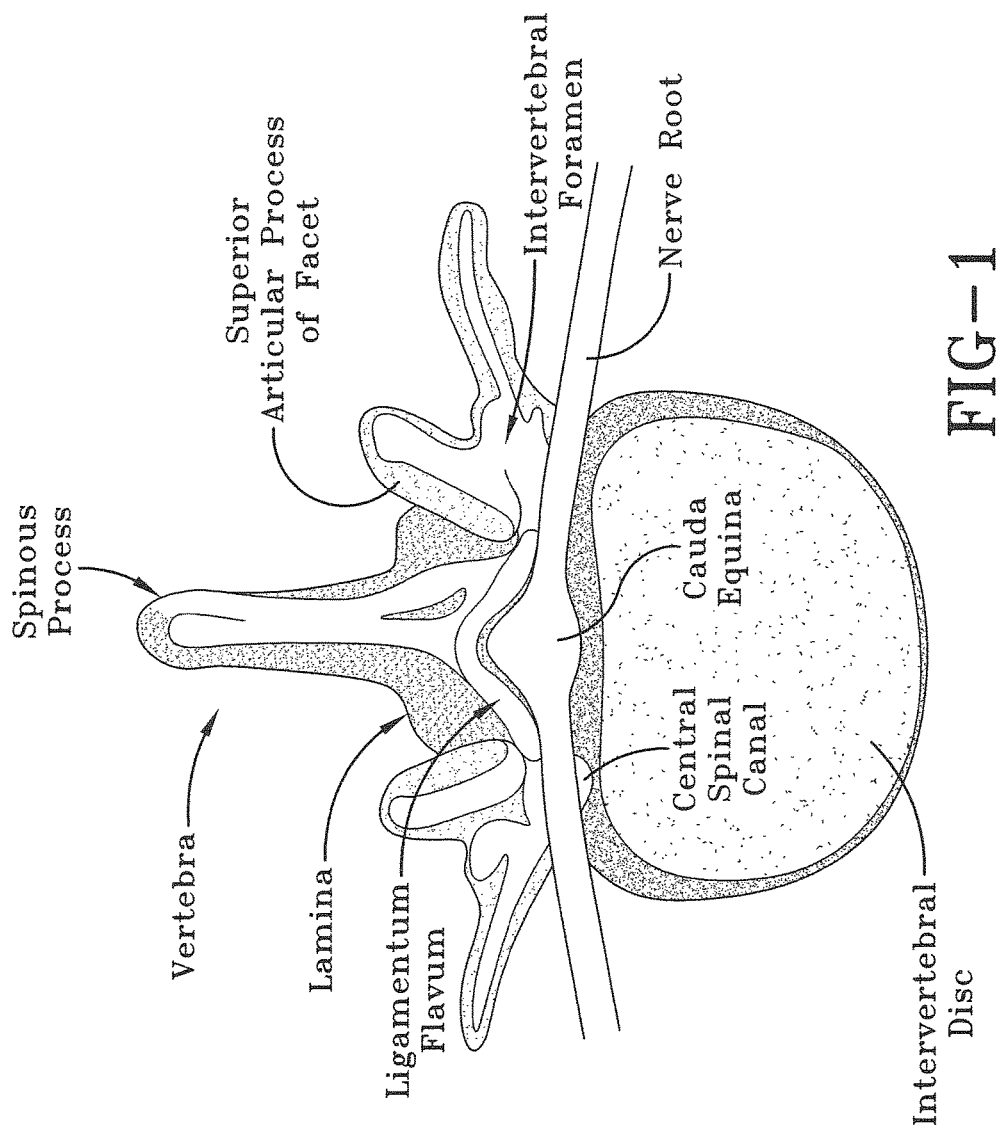
FIG. 1 is a cross-sectional view of a spine, showing a top view of a lumbar vertebra, a cross-sectional view of the cauda equina, and two exiting nerve roots.
Figure 2:
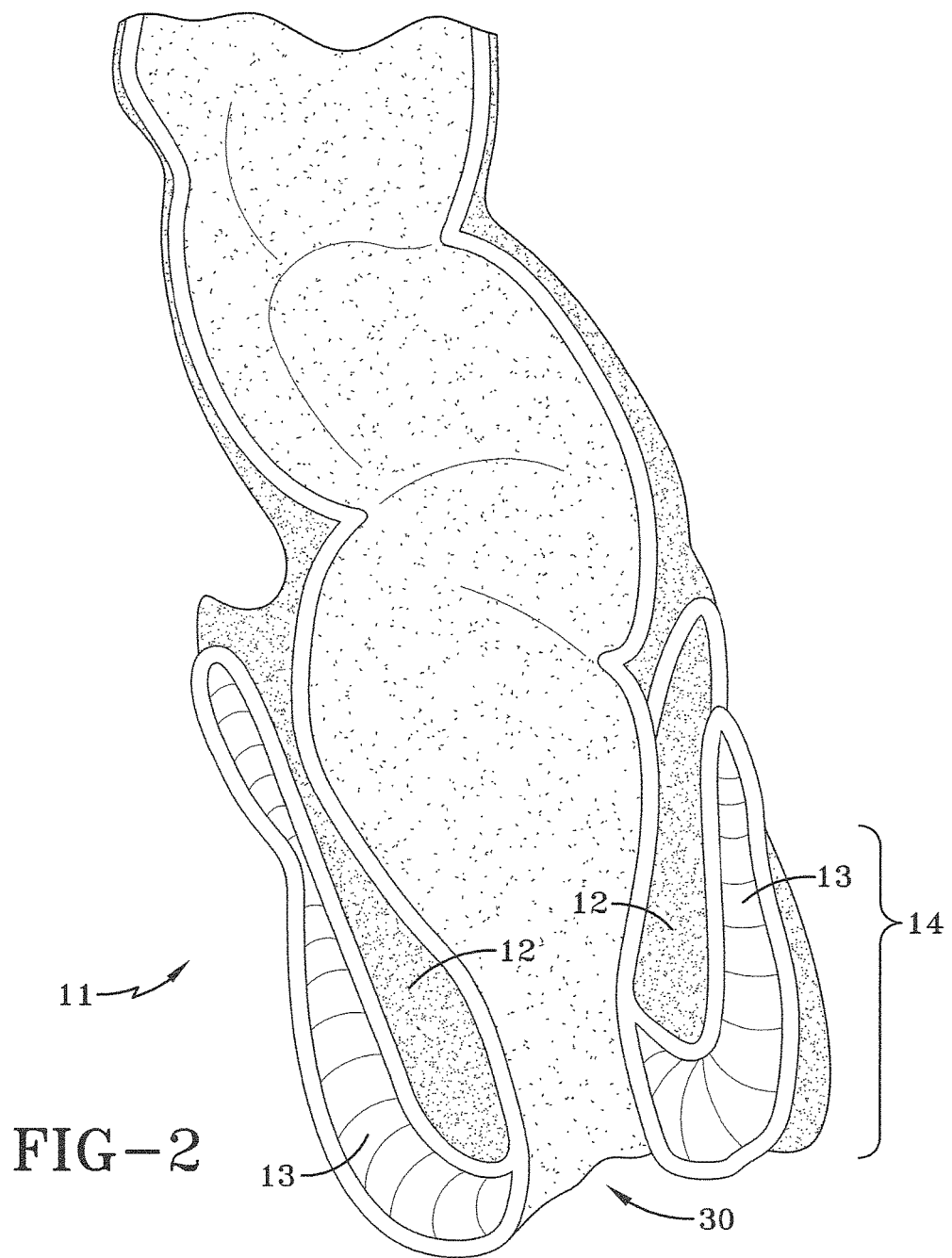
FIG. 2 is a cross sectional view of a rectum.

FIG. 2 illustrates the anatomy of a patient's rectum 11. The rectum 11 is the lower ten to fifteen centimeters of the large intestine of an adult human (this range would vary for children and various types of animals). The terminal thickening of the inner visceral smooth muscle layer of the rectal wall forms the internal anal sphincter 12, which is surrounded by the external anal sphincter 13, which together comprise the anal sphincter 14 (hereinafter also referred to herein as "the anal muscles 14"). The prostate for a male is in the shape of a donut, is just below the bladder, behind the pubic bone and just in front of the rectum. It wraps around the urethra. The outer wall of the prostate can be palpated via a digital rectal examination.

Figure 3:
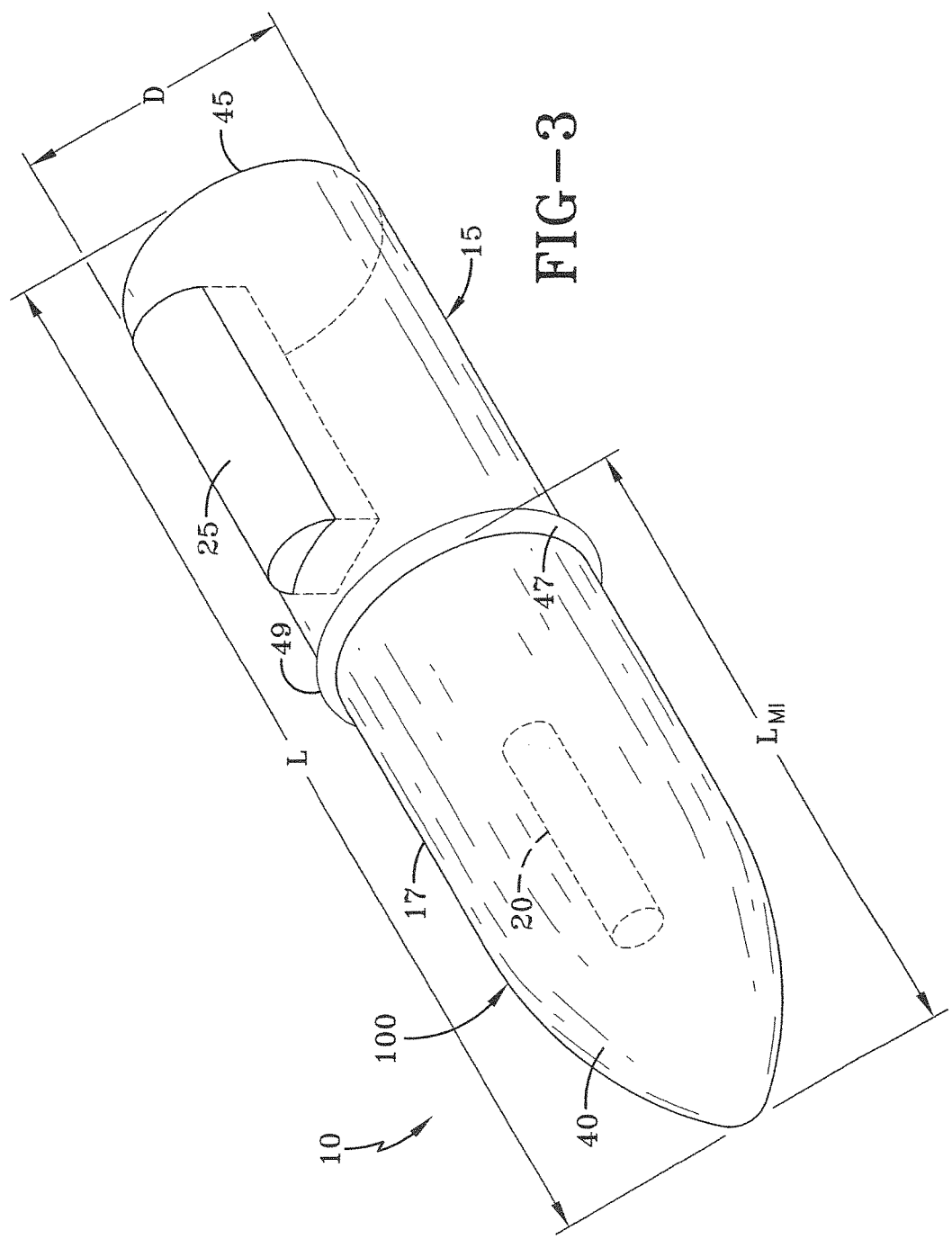
FIG. 3 is a perspective view of a probe for detecting the occurrence of cauda equina syndrome according to a first preferred embodiment of the invention.
Figure 4:
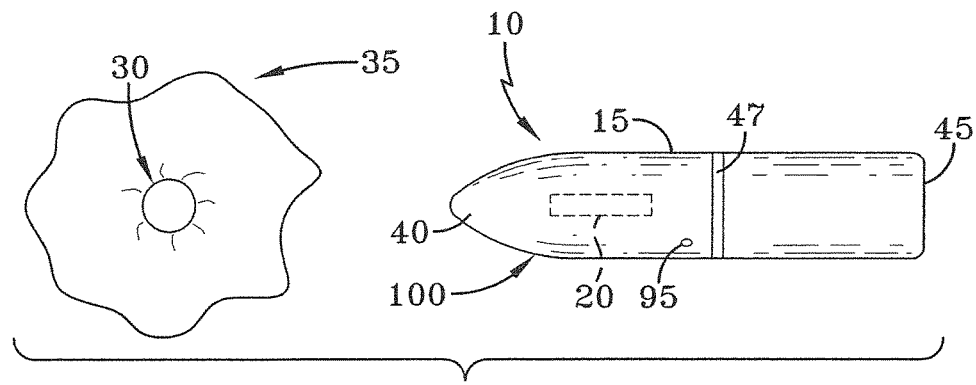
FIG. 4 is a side view of the probe shown in FIG. 3 having a sensor for measuring the pressure or force applied by a patient's anal muscles.

In a preferred embodiment of the invention as shown in FIGS. 3 and 4, a probe apparatus 10 may generally comprise a probe 100 having a body 15, a sensing device in the form of a sensor 20 and an indicating apparatus in the form of an indicator 25. The probe 100 may be inserted in an anus 30 of a patient 35 for the sensor 20 to measure the pressure and/or force (hereinafter the phrase "pressure and/or force" is referred to herein as "pressure") applied to the internal anal sphincter 12, the external anal sphincter 13, or the anal muscles 14. The indicator 25 may be capable of displaying the pressure to a physician, clinician, nurse or other medical examiner (collectively referred to herein as "examiner"). The pressure may be the actual measured pressure, such as in pounds per square inch, or whether the pressure meets, or either exceeds or is less than some threshold, where the threshold could be indicative of whether the patient has cauda equina syndrome. Although described herein with respect to the anus 30 of the patient 35, it is to be understood that the probe 100 may be used on any orifice of a human or animal (i.e., a patient) to measure the pressure applied by the surrounding tissue to the probe 100. Further, although described herein with respect to measuring the pressure applied by the anal muscles 14, it is to be understood that the probe 100 may be used to measure the pressure applied by the internal anal sphincter 12 or the external anal sphincter 13, or any combination of these muscles.

As shown in FIGS. 3 and 4, the body 15 is provided with a first or forward end 40 and a second or rearward end 45. Although shown as substantially cylindrical or fingerlike, the body 15 may have any shape to allow insertion of the first end 40 into the anus 30. Body 15 as shown in the accompanying figures has an elongated torpedo-shaped form, with a diameter D in the range of 10 to 20 mm, and a length L in the range of 20 to 200 mm. The body 15 may be provided with depth-indicating structure in the form of one or more markers 47 for indicating to the examiner the desired insertion depth for the probe 100. In a non-limiting example, the marker 47 may be a protuberance 49 as shown in FIG. 3 extending substantially perpendicularly outwardly from the body 15 a length sufficient to prevent over insertion of the body 15 into the anus 30. As shown in FIG. 3, the portion of the body 15 which is a maximum length for insertion $L_{MI}$ is shown by the numeral 17. Length $L_{MI}$ should be in the range of 5 to 10 mm, but this also may vary as did length L discussed above. These ranges could of course vary depending on the type of patient 35 in which the probe 100 is intended to be used. (There could be a set of probes 100 with different ranges of D, L and $L_{MI}$ if probe 100 could be used in a variety of patients 35.)

It is to be understood that the body 15 may be comprised of metal, polymers, plastics, composites and mixtures thereof. In a non-limiting example, the body 15 may be any material capable of undergoing sterilization procedures known in the art. It is also to be understood that a protective sheath or condom (see sheath 83 in FIGS. 16 and 17) may be provided to maintain the sterility of the body 15 to allow the body 15 to be reused. The surface of body 15 or of the sheath or condom inserted thereon should not irritate or damage the surface of the anus or whatever orifice in which it is inserted.

The sensor 20 measures the pressure applied to the probe 100 by the anal muscles 14. It is to be understood that the sensor 20 may be any sensor or transducer capable of measuring pressure including, but not limited to, mechanical sensors, electrical sensors, pneumatic sensors and combinations thereof. In a non-limiting example, the sensor 20 may be a spring-loaded sensor. Although shown as located within the body 15, it is to be understood that the sensor 20 may be located anywhere on or in the body 15 and may extend along the entire length of the body 15 or any portion thereof. As noted earlier, the pressure monitored by the sensor could be whether a threshold is met, exceeded or not.

The examiner may receive the pressure data in one or more forms such as real time during insertion, upon withdrawal, or after the patient 35 has left the exam room. As shown in FIG. 3, the indicator 25 may be provided on the probe 100 for displaying the pressure applied by the anal muscles 14. It is to be understood that the indicator 25 may be mechanical, digital, hydraulic, pneumatic, or visual (with illumination which could vary in intensity or color with changes in pressure or changes in ranges of pressure, or an alarm light which is turned on if a threshold is met, or is not met after a time period of insertion of the probe 100) or the like.

Figure 5:
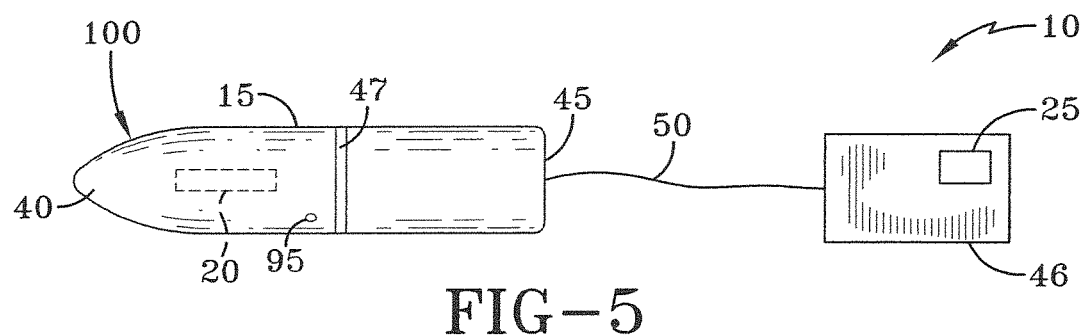
FIG. 5 is a side view of the a probe apparatus having the probe shown in FIGS. 3 and 4 connected to a remote indicator or computer responsive to the output signals of the probe shown in FIGS. 3 and 4.
Figure 6:
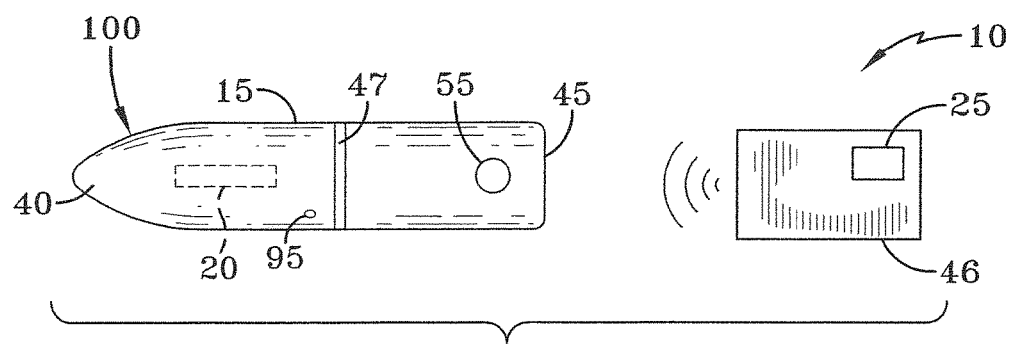
FIG. 6 is a side view of the a probe apparatus with the probe of FIGS. 3-5 having a wireless connection to a remote indicator or computer.

It is to be understood that such data, or portions or reductions thereof, may be recorded or communicated over a wired or wireless network and may also or instead be stored onboard the probe 100 of probe apparatus 10 itself, or recorded or communicated in several ways at once. In a non-limiting example, as best shown in FIG. 5, the probe apparatus 10 may include probe 100 connected to a remote indicator 25 (for example, on a computer 46) via a cord 50 (or done wirelessly), the latter components being part of probe apparatus 10. Accordingly, the data may be automatically saved as part of the patient's 35 medical record. As best shown in FIG. 6, the probe apparatus 10 may include a wireless transmitter 55 (such as a radio frequency identification or "RFID" tag) for transmitting the data to the computer 46 and/or the indicator 25.

It is to be understood, however, that the probe apparatus 10 may or may not require a control console, depending on whether battery powering is used and whether an off-board computer is used to receive the data. It is to be understood that the probe apparatus 10 may be powered via a cord or may have its own battery or power source therein (not shown). It is to be understood that the probe apparatus 10 may be capable of insertion of the probe 100 and/or other parts of probe apparatus 10 into a docking station (not shown) after use, to provide data extraction, probe sterilization/cleaning or probe recharging, for example. The probe apparatus 10 could be capable of several sources of electrical power, if electrical power is necessary for the operation of the probe apparatus, so that the probe apparatus 10 could be used in a hospital emergency room or in a location remote from electrical transmission as where a battery could be used.

As shown in FIG. 7, the probe apparatus 10 may be provided with include a handle 65 for facilitating insertion of probe 100 into anus 30 and removal of the body 15 from anus 30 by the examiner. The handle 65 may be ergonomically shaped and be made of any suitable material including, but not limited to, metals, polymers, composites and mixtures thereof. Handle 65 has a stem 81 affixed thereto for being received by a bore in body 15. The arrow near stem 81 indicates the direction handle 65 must be moved for removal from body 15. In a non-limiting example, the handle 65 may be capable of undergoing sterilization procedures known in the art to allow the handle 65 to be reused. Handle 65 could also be covered with a removable sheath (such as sheath 83 shown in FIGS. 16 and 17) and, of course, the examiner using probe apparatus 10 would ordinarily use sanitary gloves.

As best shown in FIG. 8, the handle 65 may be removably secured to the body 15. For example, after the body 15 has been inserted and removed from the anus 30, the body 15 may be disconnected from the handle 65 for disposal. It is to be understood that the handle 65 may then be sanitized and reused. Since handle 65 may have computer components and an indicator (such as indicator 25 therein), it would usually be economical to save handle 65 for reuse. Body 15 could be disposable, or it too could be sanitized for reuse. Of course, in some instances the body and the handle could be disposed. The handle 65 may be removably secured to the body 15 with a latch, clamp, pin, or the like. In a non-limiting example, the handle 65 may be provided with a trigger or button 68 that may be actuated to disconnect the handle 65 from the body 15. There also could be a ball and receptacle structure in the body 15 and handle 65 to establish the exact position at which body 15 and handle 65 are removably attached.

Figure 9:
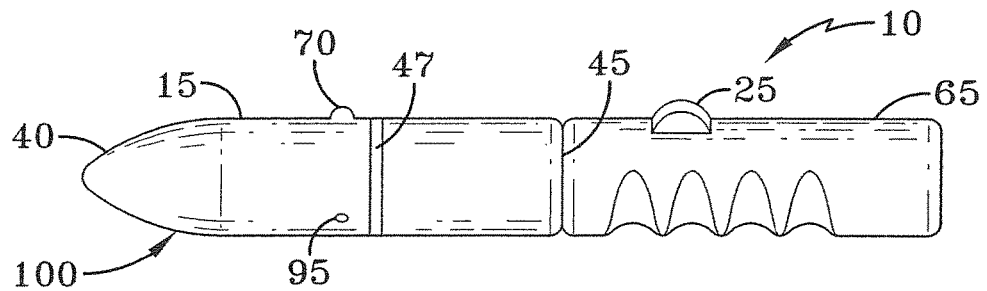
FIG. 9 is a side view of a variation of the preferred embodiment of the invention showing a probe apparatus with a probe having a perianal or rectal sensation device for detecting cauda equina syndrome.

In the variation as shown in FIG. 9, the probe 100 may be provided with a perianal sensation device 70 (hereinafter "the device 70") for engaging the perianal area surrounding the inside and/or outside of the anus 30 and/or the tissue along the anal muscles 14 to provide a sensory examination. Although shown as a protrusion in FIG. 9, it is to be understood that the device 70 may be any shape and configuration capable of engaging the perianal area and/or the tissue along the anal muscles 14. Illustrative examples include, but are not limited to, one or more ridges, indentations, grooves, needles, pins, temperature elements and combinations thereof. The device 70 may be secured to, or integral with, the body 15 and may be made from any material including, but not limited to metals, plastics, rubber, composites and the like. Device 70 could operate in other ways as described below.

Figure 10A:
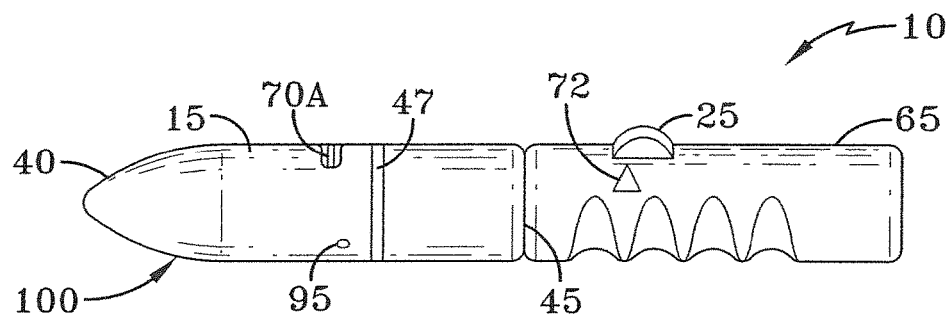
FIG. 10A is a side view of a probe apparatus with the probe as shown in FIGS. 3-5 having a perianal sensation device in a first position.
Figure 10B:
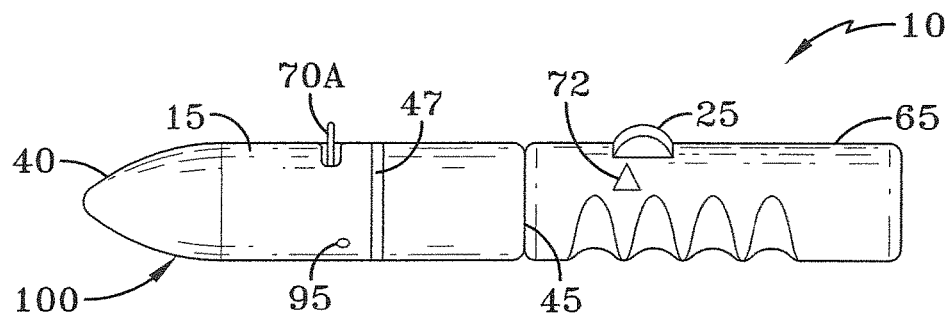
FIG. 10B is a side view of a probe apparatus showing the probe as shown in FIG. 10A having a perianal sensation device in a second position.

A variation of the device 70 is a device 70A shown in FIGS. 10A and 10B. In an illustrative example, the device 70A may be movable from a first (inactive or non-engagement) position as shown in FIG. 10A to a second (active or engagement) position as shown in FIG. 10B. It is to be understood that when in the second position, the device 70A is capable of engaging the perianal area of the patient 35. An actuator 72, such as a switch, trigger, button or the like, may be provided to move the device 70 to the first position to the second position and/or vice versa. In a non-limiting example, the device 70 (and 70A) may be calibrated to apply a predetermined amount of pressure to the perianal area upon manipulation of the actuator 72. In a non-limiting example, the device 70 (and 70A) may automatically return to the first position (such as after a predetermined period of time after insertion) from the second position, for example, to facilitate withdrawal of the body 15 from the anus 30.

Figure 12A:
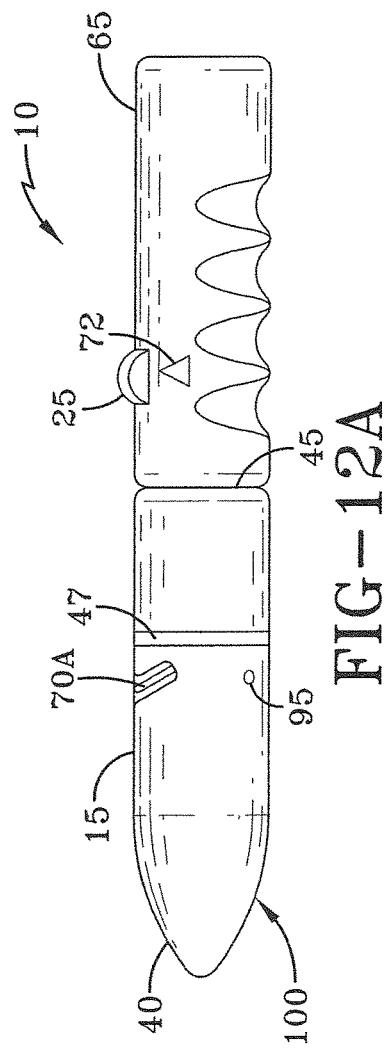
FIG. 12A is a side view of a probe apparatus according to another variation of the preferred embodiment of the invention with a probe having a perianal sensation device in a first position.
Figure 12B:
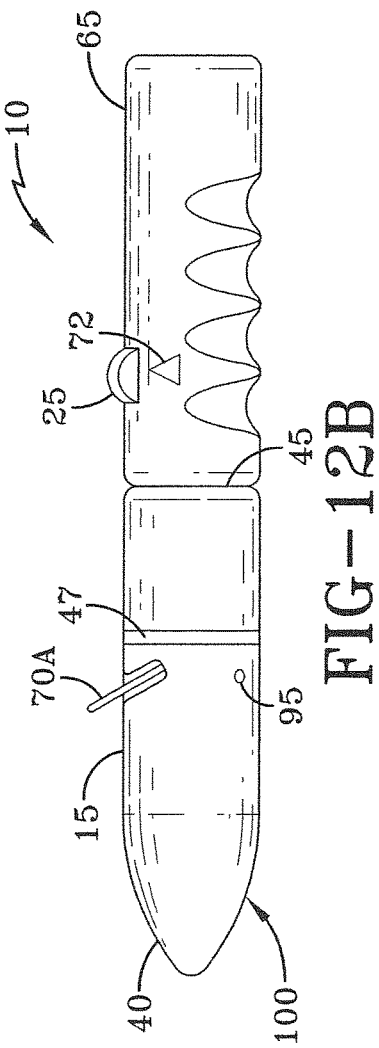
FIG. 12B is a side view of the probe apparatus shown in FIG. 11A with the probe having a perianal sensation device in a second position.

Although shown as extending substantially perpendicularly outward from the body 15 in FIGS. 10A and 10B, it is to be understood that the device 70 may be extended outwardly at any angle from the body 15. In a non-limiting example, the device 70 may be extended outward from the body 15 toward the first end 40 from a first (non-engagement) position as shown in FIG. 12A to a second (engagement) position as shown in FIG. 12B. Although shown as substantially straight in shape, the device 70 may be provided in a variety of shapes. In a non-limiting example, the device 70 may be curved, for example, to facilitate engagement with the perianal area of the patient 35.

A reduced or lack of sensation reported by the patient 35 in response to the heating or cooling of the device 70 may indicate to the examiner that the patient 35 may be at risk of cauda equina syndrome. In a non-limiting example, the device 70 may be a temperature element for use in temperature sensory examinations. The temperature element may be secured to or integral with the body 15 and capable of heating and/or cooling. It is to be understood that the probe apparatus 10 may be connected to a power source (not shown) or house a battery (not shown) to operate the device 70, if the probe apparatus 10 is electrically powered. In a non-limiting example of a temperature sensory examination, the probe 100 of probe apparatus 10 may be inserted adjacent to or in the rectum 11 of the patient 35 to contact the device 70 with the patient's 35 tissue (including, but not limited to the perianal area and/or the anal muscles 14). The device 70 may be actuated with, for example, a button or switch (not shown) to heat or cool to a desired temperature. Fluid pressure devices are also within the scope of the invention, as are devices 70 which could emit an electrical signal, a temperature signal or a painful stimulus/stimuli (or any other stimulus/stimuli which hereinafter are referred to as stimulus/stimuli) to which the perianal muscles could react, which could, for example, be used on animals.

The patient 35 may indicate to the examiner the location that the patient 35 felt the sensation in response to the heating or cooling of the device 70. A position indicator 75 (FIG. 11) for indicating the position of the device 70 on body 15 may confirm to the examiner that the patient 35 correctly identified the location (e.g., that the stimulus/stimuli was felt on the right or left side of the perianal or rectal area in order to test bilateral sensation).

Figure 11:
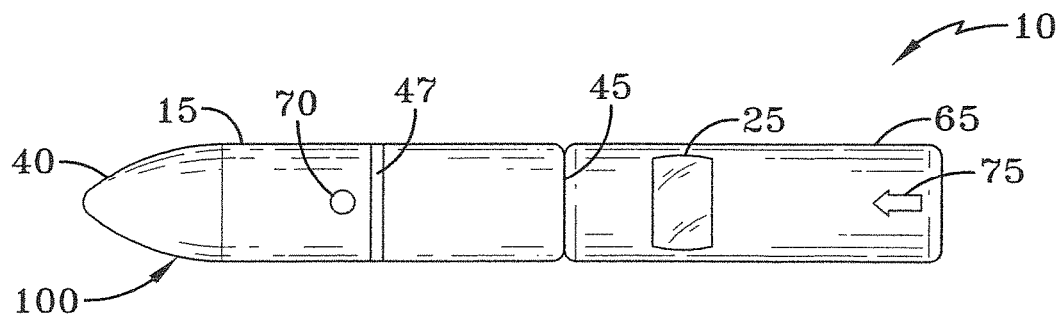
FIG. 11 is a top view of a probe apparatus with a probe as shown in FIGS. 3-5, 10A and 10B having a perianal sensation device and a location indicator according to a variation of the preferred embodiment of the invention.

As shown in FIG. 11, the probe apparatus 10 may be provided with the position indicator 75 to indicate the position of the device 70 to the examiner while the probe 100 is inserted in the anus 30. Although shown as an arrow, it is to be understood that the position indicator 75 may be any indicia, light or the like.

In an embodiment as shown in FIG. 13, the probe 100 may be provided with a diagnostic element 80 (hereinafter referred to as the "diagnostic 80") on or in the body 15 for diagnostic tests including, but not limited to, fecal occult blood testing. In a non-limiting example, the diagnostic element 80 may be a substrate (such as paper) attached to a thin film coated with guaiac (or guiack) for performing a stool guaiac test. Although shown as secured to the body 15 on or near the first end 40, it is to be understood that the diagnostic 80 may be secured anywhere on or in the body 15. It is also to be understood that the diagnostic 80 may be integral with the body 15.

In a non-limiting example of a stool guaiac test, the probe 100 may be inserted in the rectum 11 of the patient 35 to contact the diagnostic element 80 with any stool present therein. Upon removal, the diagnostic element 80 may be contacted with an oxidizer (such as peroxide). If blood is present in the sample of stool, the mixing of the fecal matter containing blood with the oxidizer on the diagnostic element 80 may cause the guaiac (or guiack) to turn a visible color. Such testing may be used to detect blood loss in the gastrointestinal tract that may be indicative of, for example, peptic ulcers or a malignancy such as cancer. Although not shown, it is to be understood that the diagnostic element 80 may be provided with a removable cover to, for example, protect the diagnostic 80 from contamination prior to use.

In an embodiment as shown in FIG. 14, the probe 100 off the probe apparatus 10 may be provided with an enlargement and/or irregularity sensor 90 for detecting irregularities and enlargements, such as irregularities and/or enlargements of the prostate which could be indicative of a diseased prostate. Other irregularities could be detected as well. The enlargement and/or irregularity sensor 90 may be secured to or otherwise integral with the body 15. The enlargement and/or irregularity sensor 90 is also referred to as a prostate topography sensor. The term "irregularity" hereinafter means irregularity and/or enlargement. The prostate topography sensor 90 could be any device for physically engaging the prostate of a male patient and could be a type of feeler device, a balloon for engaging the prostate for measuring irregularities and/or enlargement of the prostate, and the emission of sound, light or other waves of different wavelengths with a device for measuring their echo—and hence the shape or size of the prostate.

As shown in FIGS. 4-9, 10A, 10B, 12A, 12B and 13-15, the probe 100 may be provided with a thermometer 95 for measuring the temperature of the patient 35. The thermometer 95 may be secured to or integral with the body 15. It is to be understood that any thermometer known in the art may be used with the probe 100. A temperature indicator (not shown) may be provided to indicate to the examiner the temperature measured with the thermometer 95. The temperature indicator may be provided on the probe apparatus 10 for displaying the temperature. It is to be understood that the temperature indicator may be mechanical, digital or the like and that the temperature may be recorded or communicated over a wired or wireless network and may also or instead be stored onboard the probe 100 or other parts of probe apparatus 10 itself. An alarm (not shown) may be provided to indicate to the examiner to take the temperature reading.

Figure 15:
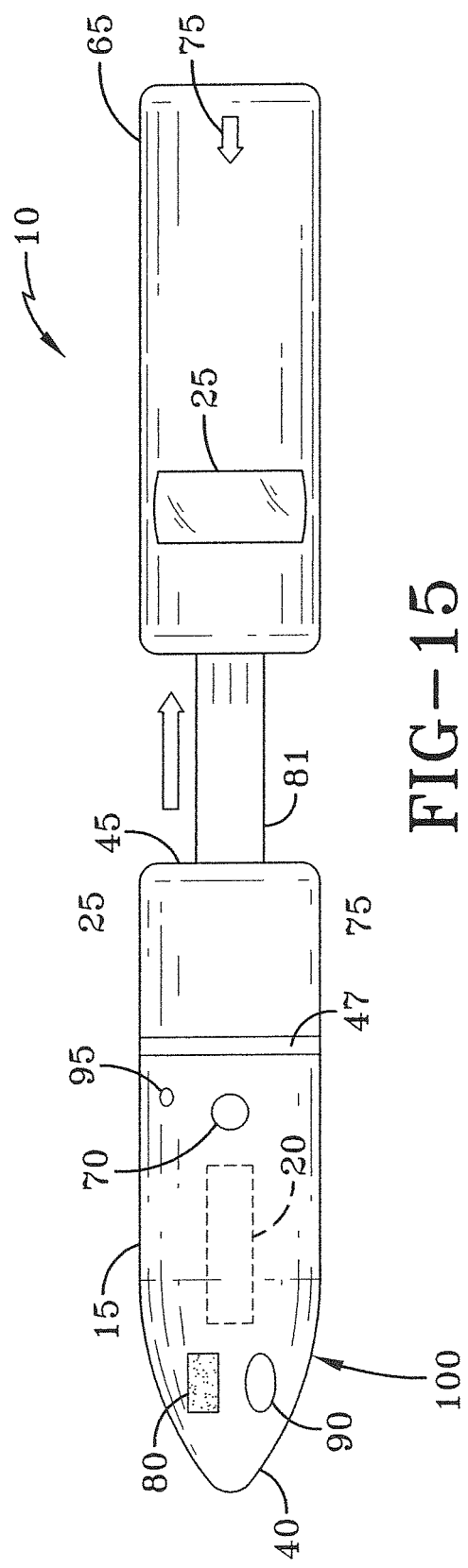
FIG. 15 is a top view of still another variation of the preferred embodiment of the invention illustrating a probe apparatus with a probe having a sensor for measuring the pressure or force applied by a patient's anal muscles and a perianal sensation device, as well as a diagnostic element, an irregularity detector, and a thermometer.

In an embodiment as shown in FIG. 15, the probe 100 of the probe apparatus 10 may be provided with the sensor 20, the device 70, the diagnostic 80, and the irregularity detector 90. It is to be understood, however, that the probe 100 may be provided with the sensor 20, the device 70, the diagnostic 80, and the irregularity detector 90 alone or in any combination thereof.

Turning to the probe apparatus 10, an example of how to use the probe apparatus 10 is illustrated in FIGS. 3-9, 10A, 10B, 11, 12A, 12B and 15-17 is set forth below. In use, the body 15 may be covered with condom or sheath 83, as mentioned above (and shown in FIGS. 16 and 17), and lubricated with a gel. The examiner may hold the second end 45 of the probe 100 (or handle 65 of probe apparatus 10, if provided) and insert the body 15 into (or adjacent) the anus 30 of the patient 35.

Figure 16:
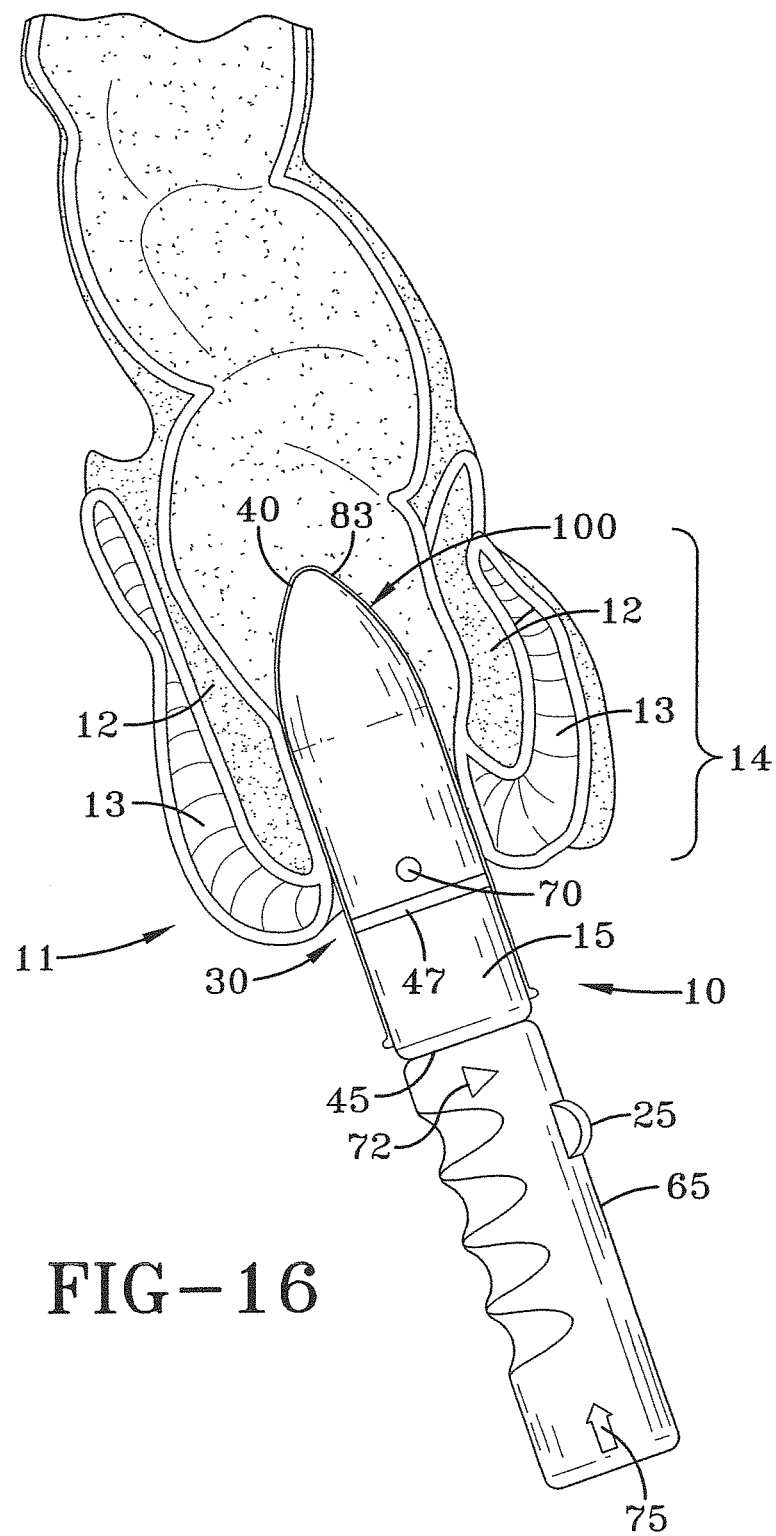
FIG. 16 is a cross sectional view of a rectum with a probe apparatus with a probe having a handle according to a preferred embodiment of the invention inserted therein.
Figure 17:
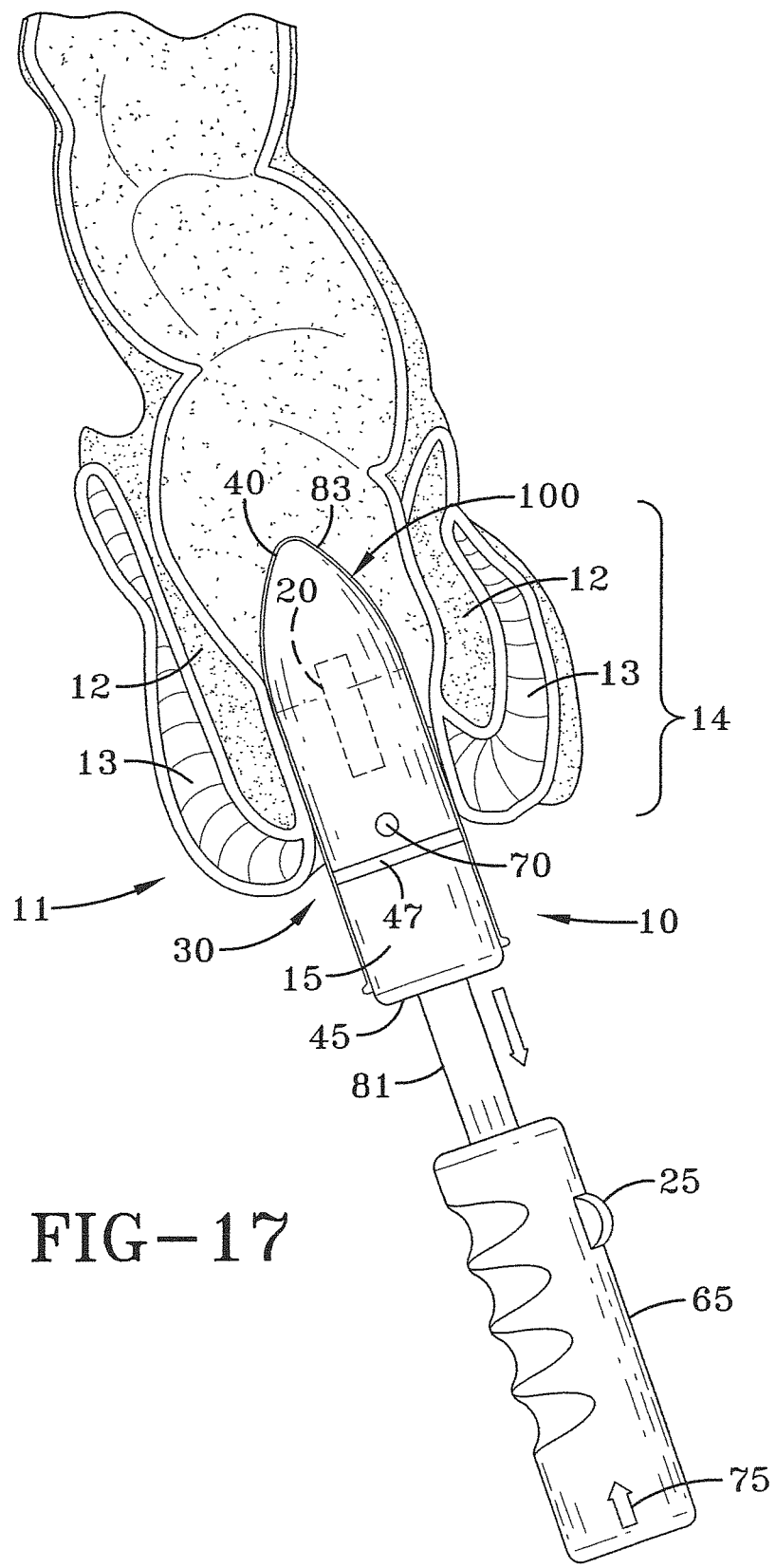
FIG. 17 is a cross-sectional view of a rectum with a probe apparatus with a probe therein having a handle being removed from a probe body according to a preferred embodiment of the invention.

A rectal or perianal tone examination may be performed with the probe 100 as shown in FIGS. 4-8 and 15-17. As best shown in FIGS. 16 and 17, the body 15 may be inserted into the anus 30 of the patient 35 to a depth to allow the sensor 20 to measure the pressure exerted by the anal muscles 14. The desired depth of insertion may be visibly indicated on the probe 100, for example, with the marker 47, or with a selected depth if a number of markers 47 are provided. In a non-limiting example, the pressure exerted by the anal muscles 14 of the patient 35 may be measured at rest (while the anal muscles 14 are not flexed) and/or while the anal muscles 14 are flexed (or attempted to be flexed) by the patient 35. The resulting pressure data may be displayed on the indicator 25. If the pressure applied by the anal muscles 14 is abnormal, the patient 35 may undergo further diagnostic tests or treatment for cauda equina syndrome.

A perianal sensory examination may be performed with the probe 100 as shown in FIGS. 9, 10A, 10B, 11 and 15-17. As best shown in FIGS. 16-17, the body 15 may be inserted into the anus 30 of the patient 35 to a depth to allow the device 70 to engage the perianal area of the patient 35. The desired depth of insertion may be visibly indicated on the probe 100, for example, with the marker 47. It is to be understood, however, that the body 15 need not be inserted in the anus 30 to perform the perianal sensory examination. In a non-limiting example, the device 70 may be positioned on (or within) the body 15 to allow the device 70 to engage the perianal area of the patient 35 when the first end 40 is positioned substantially adjacent the anus 30. A reduced or lack of sensation reported by the patient 35 in response to the engagement of the device 70 with the perianal area indicates to the examiner that the patient may be at risk of cauda equina syndrome. The patient 35 may indicate to the examiner the location that the patient 35 felt the sensation in response to the engagement of the device 70 with the perianal area. Position indicator 75 may confirm to the examiner the location the device 70 engages the perianal area to determine if the patient 35 correctly identified the location (e.g., right or left, superior or inferior).

FIG. 17 shows probe 100 inserted into anus 30 with handle 65 of probe apparatus 10 being removed. However, in reality handle 65 would not be removed from body 15 until after withdrawal of body 15 from anus 30. Once body 15 is removed, sheath 83 would be removed from body 15, and body 15 and handle 65 would be sanitized for reuse.

Figure 18:
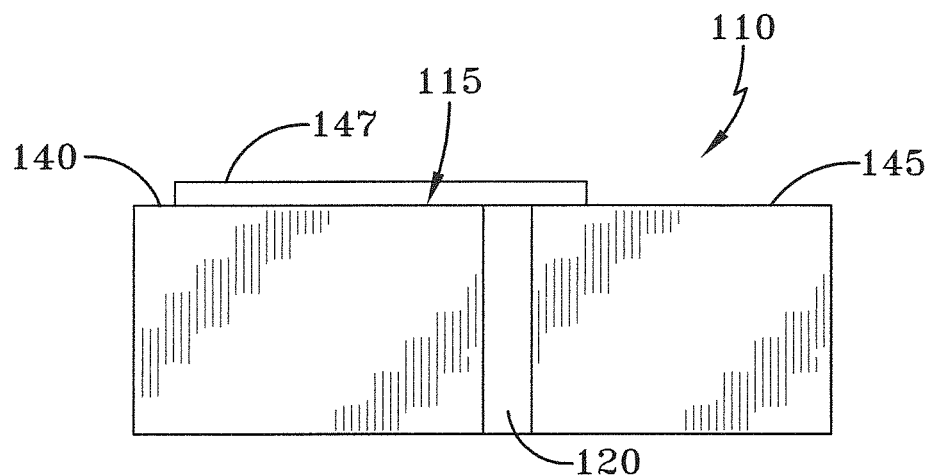
FIG. 18 is a side view of a basic form of the preferred embodiment of a rectal tone probe in schematic form.

The preferred embodiment of the invention as specifically used to measure rectal tone for diagnosing cauda equina syndrome is shown schematically in FIG. 18. In its basic form, the inventive probe 110 has a first or forward end 140 and a second or rearward end 145 at opposite ends of a body 115. Body 115 has a rectal tone sensor 120 for monitoring the rectal tone of the anus 30 of a patient 35 into which body 115 has been inserted. Sensor 120 determines whether patient 35 has cauda equina syndrome or if there is a risk of cauda equina syndrome being present. There are a number of types of sensors 120 available for measuring rectal tone as discussed earlier. Body 115 can be a variety of types for the effective insertion of body 115 into the anus 30. It could have different shapes for proper insertion according to the anus 30 into which it is to be inserted, and different degrees of hardness for effective insertion and appropriate flexibility it is to follow the path of anus 30. Rectal tone sensor 120 has to be positioned so that it is properly located to monitor the rectal tone, and this can in part be determined by the amount of insertion of body 115 into anus 30.

Figure 19:
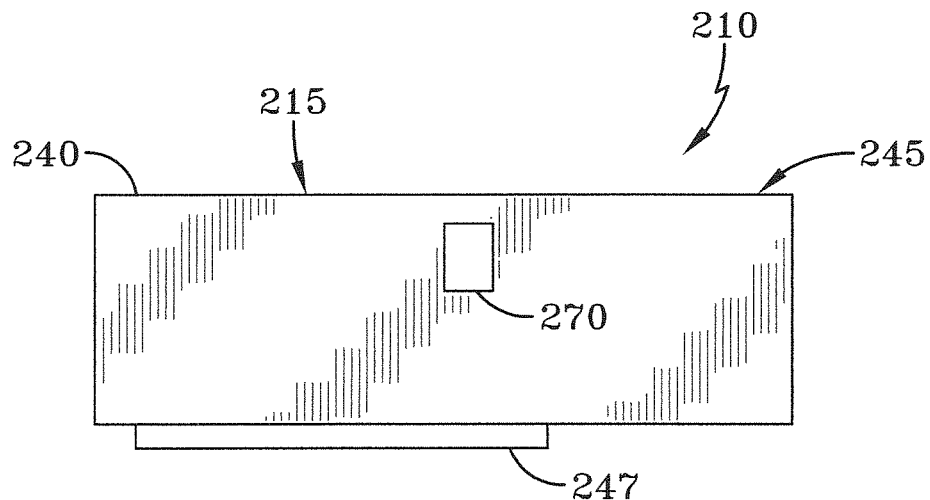
FIG. 19 is a side view of a basic form of the preferred embodiment of the invention of a perianal sensation probe in schematic form.

Another inventive probe 210 according to an aspect of the invention is shown in FIG. 19 and comprises a body 215, a first or forward end 240, a second or rearward end 245 and a perianal sensation sensor 270. Perianal sensation sensor 270 causes a stimulus/stimuli to be applied to part of the perianal area surrounding the anus 30 to determine if there is a reaction (by voice or muscle reaction). The perianal sensation sensor can cause a tactile event to the perianal area such as a pinprick, the force, pressure or impact of another protrusion (which should be moved from an active position to an inactive position as discussed earlier), or some other stimulus/stimuli to which a person without cauda equina syndrome would detect or otherwise react to such as changes in temperature (such as cold temperature, for example 50° F.), changes in pH, an electrical charge strong enough to be sensed by a patient with a healthy perianal area (or to generate a reaction such as with a person who cannot or is not able to express themselves in this regard, or an animal), and/or any other stimulus/stimuli which could normally be detected by intact perianal and/or rectal sensing organs, and the like. The features of body 215 are like those of body 115.

The force or pressure of the rectal tone determinative as to whether a patient has cauda equina syndrome or has a risk of having it is estimated to be in the range of 0 to 5 mmHg for an adult human. An appropriate electrical charge can also be applied to measure rectal tone as with electrodes administering an electric charge to the sphincter muscle and obtaining an appropriate readout. It is possible that the threshold pressure or force of the rectal tone of a patient depends on such factors as the patient's age, sex, size, particular race, etc., and if the patient is an animal (which could vary for animals as well). In order to obtain the exact thresholds to be determined and used with the probe apparatus according to the invention, evaluative tests should be taken of a statistically reliable group of patients of each of the types of possible patients. Once this is determined, the inventive probes and probe apparatus can be set accordingly, and probes and probe apparatus according to the invention can be used routinely to give fast and accurate results in an economical manner. The inventive probes and probe apparatus would be relatively easy to use and could be administered by a reasonably skilled practitioner who need not necessarily be a surgeon or other physician, but be a qualified nurse or other health care specialist. The probes and probe apparatus themselves could be made in an economical manner using known manufacturing techniques. The probes and probe apparatus could be hygienically packaged, and all or part of them could be disposable or subject to hygienic cleaning for reuse. The rectal tone test according to the invention is objective and could accurately be administered even if the patient cannot accurately describe their condition during the test or is not able to communicate at all. The routine use of the inventive probe and probe apparatus could go a long way to eliminating cauda equina syndrome and likewise to reducing or eliminating the lawsuits generated thereby.

Probes 110 and 210 can be disposable after use, can be covered with a protective covering, and have a handle as discussed earlier. The handle of the probe apparatus or probes 110 and/or 210 can be disposable or reusable in whole or in part.

Advantageously rectal tone sensor 120 and perianal sensation sensor 270 can be in the same body 115 or 215, but this is not necessary according to the present invention. FIGS. 18 and 19 show that sensors 120 and 270 can be in separate probes 110 and 210 and operate independently of each other, although certain parts such as an indicator could be shared.

As mentioned, probes 110 and 210 are most effective if sensors 120 and 270 are properly located in the anus 30. This can be done by any sort of depth-indication sensor, shown in FIGS. 18 and 19 as respective depth sensors 147 and 247. There could be markings as discussed above or any other depth defining feature.

Figure 20:
FIG. 20 is a schematic view of the operative components of the preferred form of the invention.

FIG. 20 is a schematic drawing showing the operation of versions of the preferred embodiment of the invention. The Sensing Device in one version senses the rectal tone and transmits a physical, electrical or chemical signal to a Conversion Device (which could be a transducer), which in turn transmits an input signal to an Output Device which can generate an output signal corresponding to the input signal. The output signal could be an electronic display device showing the value of the rectal tone, an alarm which is activated if the rectal tone measured is at or below the tone indicative of the presence or risk of presence of cauda equina syndrome, an appropriate colored signal such as from an illuminated light whose color changes with values of rectal tone, an audible signal or the like. The device shown in FIG. 20 could function and operate as a type of dynamometer.

Although the discussion herein has largely related to use of the inventive probe apparatus with human patients, it could be used with animals as well. The same discussion would apply as in the preceding paragraphs.

The various normal values for any of the measurements being taken according to the invention, such as cauda equina syndrome and prostate topography, are known or can be developed using various measuring techniques. These values, which could be different threshold values depending on the type of patient involved, could be used as standard values used for the probes described herein according to the invention.

Although this probe 100 and probe apparatus 10 has been shown and described with respect to a certain embodiment or embodiments, it will be apparent to those skilled in the art upon reading of this specification and the annexed drawings that many alternatives, modifications and variations may be made. In addition, while a particular feature may have been described above with respect to only one or more several illustrated embodiments, such feature may be combined with one or more other features of the other embodiments, as may be desired or advantageous for any given or particular application. Accordingly, the present invention is intended to embrace all such alternatives, modifications, variations and combinations.

I claim:

1. A method for determining whether a patient is at risk of cauda equina syndrome, said method using a probe apparatus, the probe apparatus comprising:
    a probe for insertion into the anus of the patient;
    a rectal tone sensor configured to sense the rectal tone of a patient without stimulating the anal muscles of the patient, the rectal tone sensor configured to generate a rectal tone pressure output of a rectal tone sensed, the rectal tone pressure output having a rectal tone pressure output value; and
    an indicator operatively connected to the rectal tone sensor, said indicator configured to indicate that the patient has a risk of cauda equina syndrome in the event the rectal tone pressure output value is less than a cauda equina syndrome rectal tone pressure threshold value, the cauda equina syndrome rectal tone pressure threshold value being determinative that the patient has a risk of cauda equina syndrome;

said method compromising:

inserting the probe into the anus of the patient;

checking the indicator to compare the rectal tone of the patient with the cauda equina syndrome rectal tone pressure threshold value, and determining that the patient has a risk of cauda equina syndrome when the rectal tone of the patient is less than the cauda equina syndrome rectal tone pressure threshold value.

2. A method according to claim 1 wherein the probe incorporates a diagnostic body for providing an indication that the patient has a health problem, and the method further comprising evaluating the diagnostic body after the probe has been inserted into and removed from the anus of a patient to determine whether the diagnostic body indicates that the patient has a health problem.

3. A method according to claim 1 wherein the probe comprises an irregularity sensor configured to sense irregularities and enlargement of the prostate of a male patient, and wherein the probe further has an irregularity indicator operatively connected to said irregularity sensor and configured to indicate whether the patient has an irregular or enlarged prostate, and the method further includes viewing the output of the irregularity indicator to determine whether the patient has an irregular or enlarged prostate.

4. A probe apparatus for determining whether a patient is at risk of cauda equina syndrome, said probe apparatus comprising:

a probe for insertion into the anus of a patient;

a cauda equina syndrome-detecting system comprising at least one or a combination of the following:

a rectal tone sensor operatively connectable to said probe and configured to sense the rectal tone pressure of the anal muscles of the patient without stimulating the anal muscles of the patient, said rectal tone sensor configured to generate a rectal tone pressure output in response to a rectal tone pressure sensed by said rectal tone sensor, said rectal tone pressure output having a rectal tone pressure output value;

an indicator operatively connected to said rectal tone sensor, said indicator comparing said rectal tone pressure output value both with (1) a cauda equina syndrome rectal tone pressure threshold value, said cauda equina syndrome rectal tone pressure threshold value being based on evaluative tests of patients having cauda equina syndrome, for indicating that the patient has a risk of cauda equina syndrome; and (2) a normal rectal tone pressure threshold value, said normal rectal tone pressure threshold value being determinative that the patient has a risk of cauda equina syndrome, said indicator configured to indicate that the patient has a risk of cauda equina syndrome when the rectal tone pressure value is less than the cauda equina syndrome rectal tone pressure threshold value; and a perianal sensation sensor operatively connected to said probe, said perianal sensation sensor comprising a stimulator configured to engage the perianal area of a patient, said configured to apply, a sensation-responsive stimulus/stimuli to a selected side of the perianal area of the patient.

5. A probe apparatus according to claim 4 for determining rectal tone of a patient wherein:

said indicator is responsive to said rectal tone pressure output value for indicating that the patient has a risk of cauda equina syndrome by said indicator yielding an indicating signal when the rectal tone pressure output value is less than the cauda equina syndrome rectal tone pressure threshold value.

6. A probe apparatus according to claim 4 wherein said probe apparatus comprises said rectal tone sensor and wherein said probe apparatus comprises said perianal sensation sensor.

7. A probe apparatus according to claim 6 wherein said perianal sensation sensor comprises a protrusion, said protrusion being engageable with a selected side of the perianal area of the patient to enable the determination whether the patient is sensing the engagement of said protrusion.

8. A probe apparatus according to claim 6 wherein said probe has a longitudinal axis, and said protrusion extends transversely only in one direction with respect to said longitudinal axis for engaging only one side of the perianal area of the patient.

9. A probe apparatus according to claim 7 wherein said probe is configured to move said protrusion between an inactive position and an active position, said inactive position being a position wherein said protrusion is not engageable with the perianal area of a patient, said active position being a position wherein the patient could sense said protrusion is engaging the one side of the perianal area of the patient.

10. A probe apparatus according to claim 4 wherein said stimulator applies said stimulus/stimuli to the selected side of the patient, said stimulus/stimuli being selected from the group consisting of heat, cold, electric current and a tactile stimulus/stimuli.

11. A probe apparatus according to claim 6 and further including a position indicator on said probe to indicate the position of said perianal sensation sensor upon insertion of said probe into the anus of the patient, for the patient to indicate the position of said perianal sensation sensor where the patient sensed the stimulus/stimuli applied by said stimulator.

12. A probe apparatus according to claim 5 wherein said rectal tone sensor is a pressure sensor configured to sense the pressure of at least one of the internal anal sphincter, the external anal sphincter and the perianal muscles.

13. A probe apparatus according to claim 4 wherein said indicator yields an indicating signal in the event that said rectal tone pressure output value is less than the cauda equina syndrome rectal tone pressure threshold value.

14. A probe apparatus according to claim 4 wherein said probe apparatus further comprises:

a converter operatively connected to said rectal tone sensor, said converter configured to generate an input signal corresponding to said rectal tone pressure output value generated by said sensing device; and wherein said indicator comprises an output device operatively connected to said converter, said output device generating an output signal in response to said input signal fox indicating whether the patient has a risk of cauda equina syndrome.

15. A probe apparatus according to claim 4 and further including a position indicator on said probe, said position indicator being operatively connected to a selected one of said rectal tone sensor and said perianal sensation sensor or connected to said rectal tone sensor and said perianal sensation sensor, and said position indicator comprising at least one marker on said probe, said marker indicating that the depth of insertion of said probe into the anus of the patient is sufficient for an accurate functioning of said rectal tone sensor.

16. A probe apparatus according to claim 4 wherein said probe further includes a position indicator being operatively connected to a selected one of said rectal tone sensor and said perianal sensation sensor or connected to said rectal tone sensor and said perianal sensation sensor, and said position indicator indicating (a) that the depth of insertion of said probe into the anus of a patient is sufficient for an accurate sensing of the rectal tone pressure of the patient in the event that said probe is inserted into the anus of a patient for enabling said rectal tone sensor to sense the rectal tone pressure of the patient and (b) that the depth of insertion of said probe into the anus of the patient is sufficient for said stimulator of said perianal sensation sensor to apply stimulus/stimuli to the perianal area of the anus of the patient in the event said probe is inserted into the anus of a patient to enable determining if the patient sensed the stimulus/stimuli.

17. A probe apparatus according to claim 4 wherein said rectal tone sensor is an electronic sensor, and wherein said indicator is an electronic indicator.

18. A probe apparatus according to claim 4 wherein said indicator generates an indicating signal in response to said rectal tone pressure value, said rectal tone pressure value being indicative of the strength of the anal muscle.

19. A probe apparatus according to claim 4 wherein said probe further includes a diagnostic for performing a diagnostic test.

20. A probe apparatus according to claim 19 wherein said diagnostic performs occult blood testing.

21. A probe apparatus according to claim 19 wherein said diagnostic is a substrate attached to a film coated with guaiac, said guaiac being coated on said film for performing a stool guaiac test.

22. A probe apparatus according to claim 4, said probe apparatus further comprising an irregularity sensor operatively connected to said probe and configured to detect irregularities in the internal organs of the patient.

23. A probe apparatus according to claim 22 wherein said irregularity sensor is configured to sense irregularities of the prostate of the patient when a patient is a male patient.

24. A probe apparatus according to claim 4 and further including a handle attached to said probe, said handle facilitating insertion of said probe into the anus of the patient.

25. A probe apparatus according to claim 24 wherein said handle is removable from said probe.

26. A probe apparatus according to claim 4 and further comprising both a thermometer operatively connected to said probe and configured to sense the rectal temperature of the patient, and a temperature indicator operatively connected to said thermometer, said temperature indicator indicating the sensed rectal temperature.

27. A probe apparatus according to claim 4 and further including a removable sheath for covering said probe during use of said probe, said sheath being removable and discardable after use of said probe.

28. A probe apparatus according to claim 17 wherein said indicator includes an optical display, said optical display indicating when the electronic output rectal tone pressure value is less than the cauda equina syndrome rectal tone pressure threshold value.

29. A probe apparatus according to claim 4 wherein said probe comprises a marker configured to indicate a depth of said probe for preventing over insertion of said probe into the anus of a patient to prevent said probe from injuring the patient.

30. A probe apparatus according to claim 4 wherein said stimulator comprises a protrusion extending from said probe, said protrusion being engageable with the perianal area of the patient for the patient to indicate a sensation of the engagement of said protrusion with the perianal area of the patient.

31. A method for determining from a rectal tone of a patient and a perianal sensation of a patient whether the patient is at risk of cauda equina syndrome, said method of using a probe apparatus, the probe apparatus comprising:
 a probe for insertion into the anus of the patient, the probe having operatively attached thereto the following:
 a rectal tone sensor configured to sense the rectal tone of a patient without stimulating the anal muscles of the patient, the rectal tone sensor configured to generate a rectal tone pressure output of the rectal tone sensed, the rectal tone pressure output having a rectal tone pressure output value; and
 a perianal sensation sensor, said perianal sensation sensor comprising a sensation-responsive stimulator configured to apply stimulus/stimuli to one of the right side and the left side of the perianal area of a patient to enable determining from an indication from the patient whether the patient has sensed the stimulus/stimuli; and
 an indicator operatively connected to the rectal tone sensor, said indicator being configured to respond to the rectal tone pressure output value and indicate that the patient has a risk of cauda equina syndrome in the event the rectal tone pressure output value is less than a cauda equina syndrome rectal tone pressure threshold value, the cauda equina syndrome rectal tone pressure threshold value being determinative that the patient has a risk of cauda equina syndrome;
 said method compromising:
 selectively determining whether the patient is at a risk of cauda equina syndrome by evaluating a selected one of the group consisting of a rectal tone of the patient and a perianal sensation of the patient;
 inserting the probe into the anus of the patient;
 upon selection of an evaluation of the rectal tone of the patient, checking the indicator to compare the rectal tone of the patient with the cauda equina syndrome rectal tone pressure threshold value, and determining that the patient has a risk of cauda equina syndrome when the rectal tone of the patient is less than the cauda equina syndrome rectal tone pressure threshold value; and
 upon selection of an evaluation of the perianal sensation of the patient, determining that the patient has a risk of cauda equina syndrome when the patient indicates a lack of perianal sensation when the stimulus/stimuli is applied to the one side of the perianal area of the patient.

32. A method according to claim 31 wherein the perianal sensation sensor has an inactive condition for not applying stimulus/stimuli to the perianal surface of the patient and an active condition for applying stimulus/stimuli to the perianal surface of the patient, and the method of evaluating the perianal sensation of the patient further comprises placing the perianal sensation sensor in the active condition.

33. A method according to claim 31 wherein the probe incorporates a diagnostic body for providing an indication that the patient has a health problem, and the method of evaluating a selected one of the rectal tone of the patient and the perianal sensation of the patient further comprises evaluating the diagnostic body for determining whether the diagnostic body indicates that the patient has a health problem, after the probe has been inserted into and removed from the anus of a patient to determine if the patient has a health problem.

34. A method according to claim 31 wherein the probe comprises an irregularity sensor configured to sense irregularities and enlargement of the prostate of a male patient, and wherein the probe further has an irregularity indicator operatively connected to said irregularity sensor and configured to indicate whether the patient has an irregular or enlarged prostate, and the method of evaluating a selected one of the rectal tone of the patient and the perianal sensation of the patient further includes viewing the output of the irregularity indicator to determine whether the patient has an irregular or enlarged prostate.

35. A probe apparatus for determining whether a patient is at risk of cauda equina syndrome, said probe apparatus comprising:
   a probe for insertion into the anus of a patient;
   a cauda equina syndrome-detecting system comprising at least one or a combination of the following:
   a rectal tone sensor operatively connectable to said probe and configured to sense the rectal tone pressure of the anal muscle of the patient without stimulating the anal muscles of the patient, said rectal tone sensor configured to generate a rectal tone pressure output in response to the rectal tone pressure sensed by said rectal tone sensor, said rectal tone pressure output having a rectal tone pressure output value;
   an indicator operatively connected to said rectal tone sensor, said indicator configured to compare said rectal tone pressure output value both with (1) a cauda equina syndrome rectal tone pressure threshold value, said cauda equina syndrome rectal tone pressure threshold value being based on evaluative tests of patients having cauda equina syndrome, for indicating that the patient has a risk of cauda equina syndrome; and (2) a normal rectal tone pressure threshold value, said normal rectal tone pressure threshold value being determinative That the patient has a risk of cauda equina syndrome, said indicator configured to indicate whether the patient has a risk of cauda equina syndrome when the rectal tone pressure value is less than the cauda equina syndrome rectal tone pressure threshold value to indicate that the patient does not have a risk of cauda equina syndrome when the rectal tone is equal to or above the normal rectal tone pressure threshold value; and
   a perianal sensation sensor operatively connected to said probe, said perianal sensation sensor comprising a protrusion extending from said probe and being engageable with the perianal area of a patient for applying a sensation-responsive stimulus/stimuli to a selected side of the perianal area of the patient.

36. A probe apparatus according to claim 35 wherein said rectal tone sensor is an electronic sensing device, and wherein said indicator is an electronic indicator.

37. A probe apparatus according to claim 35 for determining rectal tone of a patient wherein:
   said indicator is configured to be responsive to said rectal tone pressure output value for indicating that the patient has a risk of cauda equina syndrome by said indicator yielding an indicating signal when the rectal tone pressure output value is less than the cauda equina syndrome rectal tone pressure threshold value.

38. A probe apparatus according to claim 37 wherein said probe comprises a marker configured to indicate a depth of said probe for preventing over insertion of said probe into the anus of a patient to prevent said probe from injuring the patient.

39. A probe apparatus according to claim 35 wherein said probe apparatus comprises both said rectal tone sensor and said perianal sensation sensor.

40. A probe apparatus according to claim 35 wherein said probe has a longitudinal axis, and said protrusion extends transversely only in one direction with respect to said longitudinal axis for engaging only one side of the perianal area of the patient.

41. A probe apparatus according to claim 35 wherein said probe is configured to move said protrusion between an inactive position and an active position, said inactive position being a position wherein said protrusion is not engageable with the perianal area of a patient, said active position being a position wherein the patient could sense said protrusion is engaging the one side of the perianal area of the patient.

42. A probe apparatus according to claim 35 wherein said protrusion applies stimulus/stimuli selected from the group consisting of heat, cold, electric current and a tactile stimulus/stimuli.

43. A probe apparatus according to claim 39 and further including a position indicator on said probe to indicate the position of said protrusion upon insertion of said probe into the anus of the patient, for the patient to indicate the position of said protrusion where the patient sensed the stimulus/stimuli applied by said protrusion.

44. A probe apparatus according to claim 37 wherein said rectal tone sensor is a pressure sensor for sensing the pressure of at least one of the internal anal sphincter, the external anal sphincter and the perianal muscles.

45. A probe according to claim 35 wherein said indicator is configured to yield an indicating signal in the event said rectal tone pressure output value is less than the cauda equina syndrome rectal tone pressure threshold value.

46. A probe apparatus according to claim 35 wherein said probe apparatus further comprises:
   a converter operatively connected to said rectal tone sensor, said converter being configured to generate an input signal corresponding to said rectal tone pressure output value generated by said rectal tone sensor; and
   wherein said indicator comprises an output device operatively connected to said converter, said output device generating an output signal in response to said input signal for indicating if the patient has a risk of cauda equina syndrome.

47. A probe apparatus according to claim 35 and further including at least one marker on said probe for indicating that the depth of insertion of said probe into the anus of the patient is sufficient for an accurate functioning of said rectal tone sensor.

48. A probe apparatus according to claim 35 wherein said probe further includes depth-indicating structure for indicating a position indicator for indicating (a) that the depth of insertion of said probe into the anus of a patient is sufficient for an accurate sensing of the rectal tone pressure of the patient in the event that said probe is inserted into the anus of a patient for enabling said rectal tone sensor to sense the rectal tone pressure of the patient and (b) that the depth of insertion of said probe into the anus of the patient is sufficient for said protrusion to apply stimulus/stimuli to the perianal area of the anus of the patient in the event said probe is inserted into the anus of a patient to enable determining if the patient sensed the stimulus/stimuli.

49. A probe apparatus according to claim 36 wherein said indicator includes an optical display, said optical display indicating when the electronic output rectal tone pressure value is less than the cauda equina syndrome rectal tone pressure threshold value.

50. A probe apparatus according to claim 35 wherein said indicator is configured to generate an indicating signal in response to said rectal tone pressure value, said rectal tone pressure being indicative of the strength of the anal muscle.

51. A probe apparatus according to claim 35 wherein said probe further includes a diagnostic for performing a diagnostic test.

52. A probe apparatus according to claim 51 wherein said diagnostic performs occult blood testing.

53. A probe apparatus according to claim 51 wherein said diagnostic is a substrate attached to a film coated with guaiac, said guaiac being coated on said film for performing a stool guaiac test.

54. A probe apparatus according to claim 35, said probe apparatus further comprising an irregularity sensor, operatively connected to said probe and configured to detect irregularities in the internal organs of the patient.

55. A probe apparatus according to claim 54 wherein said irregularity sensor is configured to sense irregularities of the prostate of the patient when a patient is a male patient.

56. A probe apparatus according to claim 35 and further including a handle attached to said probe, said handle facilitating insertion of said probe into the anus of the patient.

57. A probe apparatus according to claim 56 wherein said handle is removable from said probe.

58. A probe apparatus according to claim 35 and further comprising both a thermometer operatively connected to said probe and configured to sense the rectal temperature of the patient, and a temperature indicator operatively connected to said thermometer, said temperature indicator indicating the sensed rectal temperature.

59. A probe apparatus according to claim 35 and further including a removable sheath for covering said probe during use of said probe, said sheath being removable and discardable after use of said probe.

* * * * *